US009226913B2

(12) United States Patent
Dalgleish et al.

(10) Patent No.: US 9,226,913 B2
(45) Date of Patent: Jan. 5, 2016

(54) METHODS OF TREATING CANCER USING A COMBINATION OF AN IMMUNOMODULATORY COMPOUND AND AN ARTEMISININ OR A DERIVATIVE THEREOF

(75) Inventors: Angus Dalgleish, Cheam (GB); Andrew Gravett, London (GB); Wai Liu, Old Coulsdon (GB)

(73) Assignee: Celgene Corporation, Summit, NJ (US)

( * ) Notice: Subject to any disclaimer, the term of this patent is extended or adjusted under 35 U.S.C. 154(b) by 477 days.

(21) Appl. No.: 13/520,675

(22) PCT Filed: Jan. 5, 2011

(86) PCT No.: PCT/US2011/020160
§ 371 (c)(1),
(2), (4) Date: Feb. 15, 2013

(87) PCT Pub. No.: WO2011/084968
PCT Pub. Date: Jul. 14, 2011

(65) Prior Publication Data
US 2013/0136757 A1    May 30, 2013

Related U.S. Application Data

(60) Provisional application No. 61/292,307, filed on Jan. 5, 2010, provisional application No. 61/371,347, filed on Aug. 6, 2010.

(51) Int. Cl.
| | |
|---|---|
| *A61K 31/366* | (2006.01) |
| *A61K 31/7068* | (2006.01) |
| *A61K 31/45* | (2006.01) |
| *A61K 31/4015* | (2006.01) |
| *A61K 31/282* | (2006.01) |
| *A61K 31/357* | (2006.01) |
| *A61K 31/4035* | (2006.01) |
| *A61K 31/454* | (2006.01) |
| *A61K 31/541* | (2006.01) |
| *A61K 45/06* | (2006.01) |

(52) U.S. Cl.
CPC ............ *A61K 31/366* (2013.01); *A61K 31/282* (2013.01); *A61K 31/357* (2013.01); *A61K 31/4035* (2013.01); *A61K 31/454* (2013.01); *A61K 31/541* (2013.01); *A61K 31/7068* (2013.01); *A61K 45/06* (2013.01)

(58) Field of Classification Search
CPC ........... A61K 31/3666; A61K 31/7068; A61K 31/45; A61K 31/4015; A61K 31/366
See application file for complete search history.

(56) References Cited

U.S. PATENT DOCUMENTS

| | | | |
|---|---|---|---|
| 5,635,517 A | 6/1997 | Muller et al. | |
| 5,698,579 A | 12/1997 | Muller | |
| 5,798,368 A | 8/1998 | Muller et al. | |
| 5,874,448 A | 2/1999 | Muller et al. | |
| 5,877,200 A | 3/1999 | Muller | |
| 5,929,117 A | 7/1999 | Muller et al. | |
| 5,955,476 A | 9/1999 | Muller et al. | |
| 6,281,230 B1 | 8/2001 | Muller et al. | |
| 6,316,471 B1 | 11/2001 | Muller et al. | |
| 6,335,349 B1 | 1/2002 | Muller et al. | |
| 6,380,239 B1 | 4/2002 | Muller et al. | |
| 6,403,613 B1 | 6/2002 | Man et al. | |
| 6,458,810 B1 | 10/2002 | Muller et al. | |
| 6,476,052 B1 | 11/2002 | Muller et al. | |
| 6,555,554 B2 | 4/2003 | Muller et al. | |
| 6,649,647 B1 | 11/2003 | Haynes et al. | |
| 7,091,353 B2 | 8/2006 | Robarge et al. | |
| 7,323,479 B2 | 1/2008 | Zeldis | |
| 7,393,862 B2 | 7/2008 | Zeldis | |
| 7,468,363 B2 | 12/2008 | Zeldis | |
| 7,968,569 B2 | 6/2011 | Zeldis | |
| 8,188,118 B2 | 5/2012 | Zeldis | |
| 8,198,262 B2 | 6/2012 | Zeldis | |
| 8,198,306 B2 | 6/2012 | Zeldis | |
| 8,207,200 B2 | 6/2012 | Zeldis | |
| 8,410,136 B2 | 4/2013 | Zeldis | |
| 8,440,194 B2 | 5/2013 | Zeldis | |
| 8,492,406 B2 | 7/2013 | Zeldis | |
| 8,530,498 B1 | 9/2013 | Zeldis | |
| 8,623,384 B2 | 1/2014 | Zeldis | |
| 8,632,787 B2 | 1/2014 | Zeldis | |
| 8,648,095 B2 | 2/2014 | Zeldis | |
| 8,673,939 B2 | 3/2014 | Zeldis | |
| 2003/0045552 A1 | 3/2003 | Robarge et al. | |
| 2003/0096841 A1 | 5/2003 | Robarge et al. | |
| 2006/0084675 A1 | 4/2006 | Efferth et al. | |

(Continued)

FOREIGN PATENT DOCUMENTS

| | | |
|---|---|---|
| WO | WO 2007/101235 | 9/2007 |
| WO | WO 2011/012626 | 3/2011 |

OTHER PUBLICATIONS

International Search Report in corresponding PCT Application No. PCT/US2011/020160 dated Mar. 3, 2011.
Hou, J. et al., "Experimental Therapy of Hematoma with Artemisinin and its Derivatives: In vitro and In vivo Activity, Chemosensitization, and Mechanisms of Action," *Clin Cancer Res*, 2008, 14(17):5519-5530.
Buommino, E. et al., "Artemisinin reduces human melanoma cell migration by down-regulating αVβ3 integrin and reducing metalloproteinase 2 production," *Invest New Drugs*, 2009, 27:412-418.
Galustian, C. and Dalgleish, A., "Lenalidomide: a novel anticancer drug with multiple modalities," *Expert Opinion Pharmacother.*, 2009, 10(1):125-133.
Li, S. et al., "Effect of artesunate on inhibiting proliferation and inducing apoptosis of SP2/0 myeloma cells through affecting NFκB p65," *Int J Hematol*, 2009, 90:513-521.

(Continued)

*Primary Examiner* — Shengjun Wang
*Assistant Examiner* — Sahar Javanmard
(74) *Attorney, Agent, or Firm* — Jones Day

(57) ABSTRACT

Provided herein are methods for treating cancers by administering immunomodulatory compounds in combination with artemisinin or a derivative thereof. In particular, methods for treating cancers by administering lenalidomide in combination with artemisinin or a derivative thereof are provided.

7 Claims, 9 Drawing Sheets

(56) References Cited

U.S. PATENT DOCUMENTS

Figure 1:
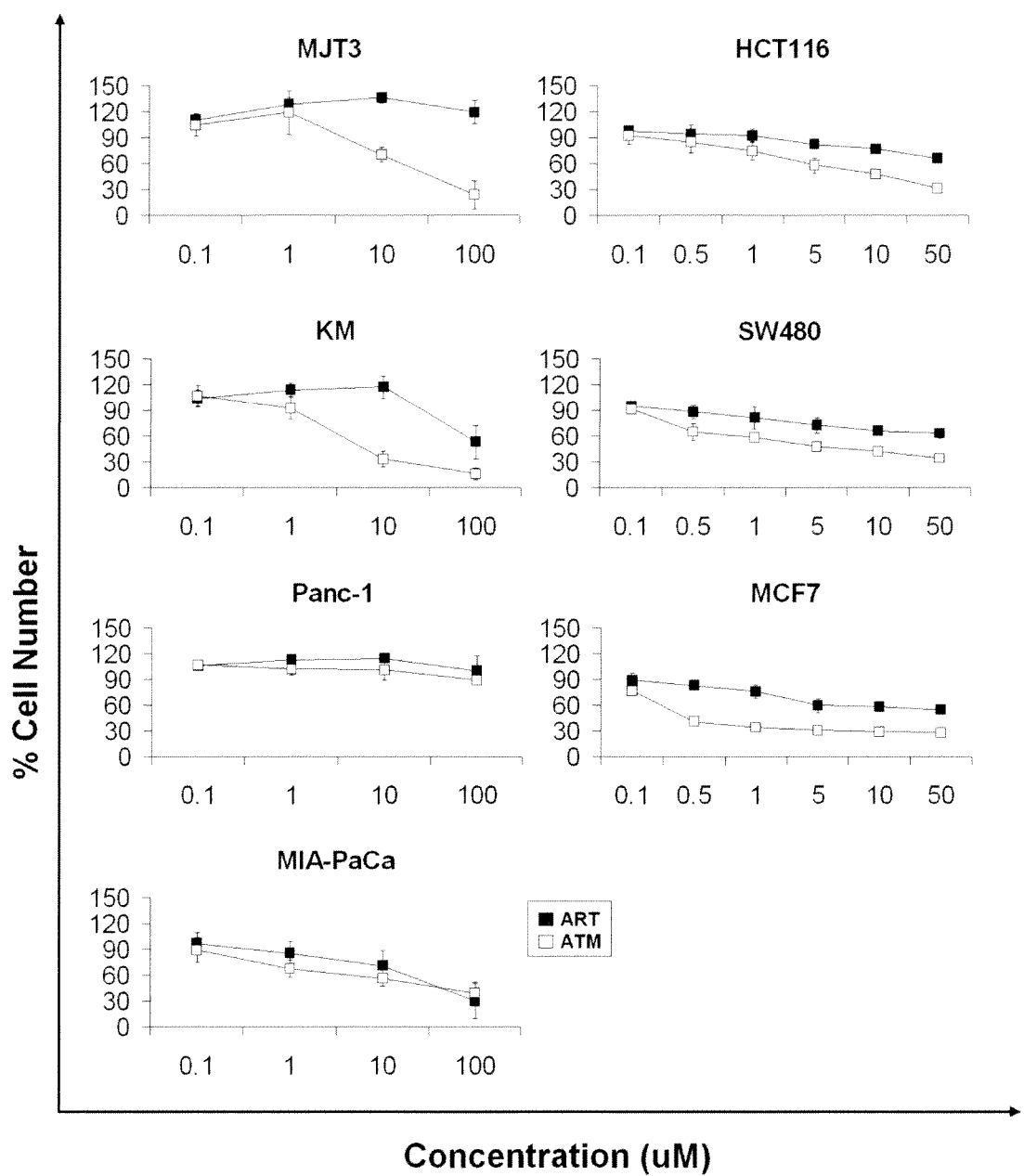

| | | |
|---|---|---|
| 2007/0049618 A1 | 3/2007 | Muller et al. |
| 2012/0035145 A1 | 2/2012 | Zeldis |
| 2012/0237595 A1 | 9/2012 | Zeldis |
| 2013/0177644 A1 | 7/2013 | Zeldis |
| 2013/0183381 A1 | 7/2013 | Zeldis |
| 2013/0302323 A1 | 11/2013 | Zeldis |

OTHER PUBLICATIONS

Office Action in corresponding EP Application No. 11700288.1 dated Apr. 3, 2014.

Li, Lin-Na et al., "Differential sensitivity of colorectal cancer cell lines to artesunate is associated with expression of beta-catenin and E-cadherin," *European Journal of Pharmacology*, 2008, 588:1-8.

Efferth, T. et al., "The anti-malarial artesunate is also active against cancer," *International Journal of Oncology*, 2001, 18:767-773.

METHODS OF TREATING CANCER USING A COMBINATION OF AN IMMUNOMODULATORY COMPOUND AND AN ARTEMISININ OR A DERIVATIVE THEREOF

The present application is a National Stage application of PCT/US2011/020160 filed Jan. 5, 2011, which published as WO 2011/084968 A1 on Jul. 14, 2011 and claims priority benefit from U.S. Provisional Application No. 61/292,307, filed Jan. 5, 2010 and U.S. Provisional Application No. 61/371,347, filed Aug. 6, 2010, all of which are incorporated herein by reference in their entireties.

1. FIELD

Provided herein are methods of treating cancer by administering immunomodulatory compounds in combination with other compounds.

2. BACKGROUND

Herbal remedies involving the Sweet wormwood (*Artemisia annua*) have been traditionally used in China as a treatment for a variety of ailments, including fever and rheumatism. The major active ingredient artemisinin was identified and isolated in the 1970s, and its particular activity as a compound targeting malaria was investigated ever since.

2.1 Artemisinins

Studies involving a structure-activity relationship analyses of the original parental artemisinin molecule have focused on developing the hemisuccinate ester of artemisinin known as artesunate (ART), which taken together with its siblings have resulted in a family of compounds collectively known as the "artemisinins." These agents are amongst the most potent and rapidly-acting anti-malarial agents known, and are efficacious against parasites that are resistant to established antimalarial drugs such as chloroquine and pyrimethamine (Li et al., 1984, *Lancet*. 2:1360-1361; Krishna et al., 2008. *Trends Phurniacol Sci*. 29:520-7). The mechanism of action of artemisinins has yet to be defined, but studies have described a role for free-radicals. Specifically, induced de novo production of reactive hydroxyl moieties and superoxides within the malarial parasite, have been reported that damages intracellular processes and causes death (Meshnick S R. 2002. *Int J Parasitol*. 32:1655-60; Golenser et al., 2006 *Int Parasitol*. 36:1427-41). In spite of the lack of a definitive mechanism, the World Health Organisation have recommended that all anti-malarial therapies should contain an artemisinin component, especially when used as a first line treatment.

There is growing evidence supporting a role of ART and other artemisinins in cancer therapy (Efferth et al., 2001, *Int Oncol*, 18:767-73; Efferth et at, 2007, *PLoS One*, 2:e693; Efferth et al., 2007, *Trends Mol Med*, 13:353-61; Li et at, 2007, *Int J Cancer;* 121:1360-5; Chen et al., 2009, *Anticancer Drugs*, 20:131-40; Du et at, 2010, *Cancer Chemother Pharmacol*, 65:895-902; Gravett et al., 2010, *Cancer Chemother Pharmacol*, [Epub ahead of print]; Michaelis et al., 2010, *Biochem Pharmacol*, 79:130-6). Anti-proliferative activity has been described in vitro for this class of agent in a wide spectrum of tumour cell lines as well as in primary material derived from patients. The mechanism(s) underlying these activities are unclear, and have included i) actions on cell cycle proteins that determine transit through G1 restriction (Hou et al., 2008, *Clin Cancer Res*, 14:5519-30); ii) disruptions to the intrinsic apoptotic pathway that it drive towards a pro-apoptotic outcome (Du et al., 2010, *Cancer Chemother Pharmacol*, 65:895-902; Michaelis et at, 2010, *Biochem Pharmacol*, 79:130-6; Zhou et al., 2008, *Anticancer Drugs*, 19:247-55); iii) anti-angiogenic and anti-metastatic properties (Anfosso et al., 2006, *Pharmacogenomics J*, 6:269-78; Zhou et at, 2007, *Vascul Pharmacol*, 47:131-8; Rasheed et al., 2010, *Int J Cancer*, 127(6):1475-85); and iv) inhibition of NF-kB (Li et al., 2009 *Int J Hematol*, 90:513-21; Li et al., 2010, *Int Immunopharmacol*, 10:344-50). The diversity in the targets of ART, naturally lends support to the possibility that it be used in combination with other agents that mutually support each other (Liu W M, 2008, *Curr Clin Pharmacol*, 3:108-17). Indeed, there were reports on non-antagonistic interactions between ART and ART-related compound with common anti-cancer drugs (Gravett et al., 2010, *Cancer Chemother Pharmacol*, [Epub ahead of print]; Li et al., 2010, *Int Immunopharmacol*, 10:344-50) as well as enhanced activities in combinations with more novel treatment modalities such as erlotinib and rituximab (Efferth et at, 2004, *Biochem Pharmacol*. 67:1689-1700: Sieber et al., 2009, *Int J Oncol*, 35:149-58).

There is currently only limited and simplistic published data exploring the value of ART as a combination partner in treatment regimens. These studies have used simple approaches to studying drug-drug interactions, and as a consequence, their conclusions are still open to debate.

2.2 Artemisinin Derivatives (ARTds)

Structure-activity relationship analyses of the original parental artemisinin molecule have also yielded a novel class of trioxanes, designated the artemisinin derivatives (ARTds), which are amongst the most potent antimalarial agents known. ARTds are thought to target multiple cellular processes within the *Plasmodium* sp. parasite that causes malaria, and for that reason can be more than a 1.000 times more effective than the more standard antimalarial treatments such as chloroquine and pyrimethamine (Haynes et al., 2006, *Angew. Chem. Int. Ed Engl*. 45, 2082-2088). Furthermore, the ARTds are much faster acting than most of these treatments (Li et al., 1984, *Lancet*, 2: 1360-1361; Li, et al., 1994, *Trans. R. Soc. Trop. Med. Hyg*. 88 Suppl 1, S5-S6), and can also clear drug-resistant strains of the parasite. These impressive qualities and activities have resulted in the World Health Organisation recommending that all antimalarials be combined with an ARTd component when used first line (WHO Guidelines for the treatment of malaria (2006)).

One notable example of a ARTd is artemisone (ATM). ATM has emerged as a therapeutic candidate and possesses sustained activity in plasma compared to sister compounds. This renders it significantly more active against the most common malarial parasite *Plasmodium falciparum* than other antimalarial drugs (Haynes et al., 2006, *Angew. Chem. Int. Ed Engl*. 45, 2082-2088; Vivas et al., 2007, *J. Antimicrob. Chemother*. 59, 658-665; Ramharter et al., 2006. *Am. J. Trop. Med. Hyg*. 75: 637-639). It has almost negligible toxicity (Nagelschmitz et al., 2008. *Antimicrob. Agents Chemother*. 52: 3085-3091), and benefits from having low production costs by being synthesised from the parental artemisinin compound in just 3-steps.

In recent years the ARTds have also been shown to have anticancer properties, through their ability to reduce cell number in a variety of solid tumours in vitro (Woerdenbag et al., 1993, *J. Nat. Prod*. 56: 849-856; Efferth et al., 2001, *Int. J. Oncol*. 18: 767-773; Chen et al. 2003, *Pharmacol. Res*. 48: 231-236; Nakase et al., 2008. *Int. J. Pharm*. 354: 28-33) and in ex vivo animal models (Li et al. 2007, *Int. J. Cancer* 121: 1360-1365). Activity has also been seen in humans (Berger et al. 2005, *Oncol. Rep*. 14, 1599-1603; Singh et al. 2006. *Integr. Cancer Ther*. 5: 391-394), and a recent phase II study in patients with lung cancer reported ARTd combinations could extend short-term survival and time-to-progression rates (Zhang et al., 2008, *Zhong. Xi. Yi. Jie. Xue. Bao.* 6: 134-138). Studies have identified several potential mechanisms for the ARTds against cancer cells. However, a single mechanism has yet to be defined. The ARTds have been shown to be anti-proliferative through that action on key cell cycle regulatory proteins such as $p21^{waf1cip1}$ and cyclin D1 (Hou et al., 2008, *Clin. Cancer Res.* 14: 5519-5530); pro-apoptotic by manipulating the Bax:Bcl-2 rheostat (Singh, et al. 2004, *Anticancer Res.* 24: 2277-2280; Zhou et al., 2008, *Anticancer Drugs* 19: 247-255); anti-angiogenic by targeting vascular endothelial growth factor (Chen et al., 2004, *Cancer Chemother. Pharmacol.* 53:423-432; Wartenberg et al., 2003, *Lab Invest.* 83: 1647-1655); and anti-migratory through their effects on $\alpha V\beta 3$ integrins (Buommino et al., 2009, *Invest New Drugs* 27: 412-418). The multi-modal character of these classically antimalarial drugs, allied to their low host toxicity even at high doses (Ribeiro et al., 1998, *Med. Trop. (Mars.)* 58: 50-53; Gordi et al., 2004, *Toxicol. Lett.* 147: 99-107), reinforce their development as a novel anti-cancer agent.

It has been known for some time that the efficacy of ARTds is significantly enhanced when used in combination with other agents, which is an approach that may be beneficial in cancer. Indeed, ARTds have already shown some synergy with common chemotherapy (Adjuik et al., 2004, *Lancet*, 363 (9402):9-17). Furthermore, cancer cells can become addicted to certain pathways, which ultimately lead to drug resistance when single agents that target specific pathways are used (Liu W M. 2008, *Curr Clin Pharmacol.*, 2:108-17). Consequently, using drugs that display a wider target-window, such as the ARTds, in combination with more established cytotoxic drugs may improve overall activity.

Citation of any references in this Section of the application is not to be construed as an admission that such references is prior art to the present application.

3. SUMMARY

Provided herein are methods and compositions for the treatment of cancer. In some embodiments, an immunomodulatory compound is administered to a patient, in combination with an artemisinin or a derivative thereof, or both. In some embodiments, the immunomodulatory compound is lenalidomide. In some embodiments, the artemisinin is artesunate. In some embodiments, the artemisinin derivative is artemisone. The combination exhibits a synergistic effect that can increase the likelihood of an effective patient response.

3.1 DEFINITIONS

As used herein, and unless otherwise specified, the terms "treat," "treating" and "treatment" refer to an action that occurs while a patient is suffering from the specified cancer, which reduces the severity of the cancer, or retards or slows the progression of the cancer.

As used herein, unless otherwise specified, the terms "prevent," "preventing" and "prevention" refer to an action that occurs before a patient begins to suffer from the specified cancer, which inhibits or reduces the severity of the cancer.

As used herein, and unless otherwise indicated, the terms "manage," "managing" and "management" encompass preventing the recurrence of the specified cancer in a patient who has already suffered from the cancer, and/or lengthening the time that a patient who has suffered from the cancer remains in remission. The terms encompass modulating the threshold, development and/or duration of the cancer, or changing the way that a patient responds to the cancer.

As used herein, and unless otherwise specified, the term "therapeutically effective amount" of a compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent.

As used herein, and unless otherwise specified, the term "prophylactically effective amount" of a composition is an amount sufficient to prevent cancer, or one or more symptoms associated with cancer, or prevent its recurrence. The term "prophylactically effective amount" can encompass an amount that improves overall prophylaxis or enhances the prophylactic efficacy of another prophylactic agent.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The terms "treatment" and "prevention" contemplate both a complete and a partial response.

"Tumor," as used herein, refers to all neoplastic cell growth and proliferation, whether malignant or benign, and all precancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth. Benign tumors generally remain localized. Malignant tumors are collectively termed cancers. The term "malignant" generally means that the tumor can invade and destroy neighboring body structures and spread to distant sites to cause death.

The terms "cancer" and "cancerous" refer to or describe the physiological condition in mammals that is typically characterized by unregulated cell growth. Examples of cancer include, but are not limited to, blood-borne tumors (e.g., multiple myeloma, lymphoma and leukemia), and solid tumors.

4. BRIEF DESCRIPTION OF THE DRAWINGS

FIG. 1. Cell viability curves in response to ART and ATM as measured by MTT assay for seven cancer cell lines. Cells were exposed to a range of drug concentrations for 72 hrs, before measuring the number of viable cells by absorbance at 550 nm. ATM decreased cell number to a greater degree than ART when used at eaui-active concentrations. Data points represent the mean and SDs of at least 3 separate experiments.

Figure 2:
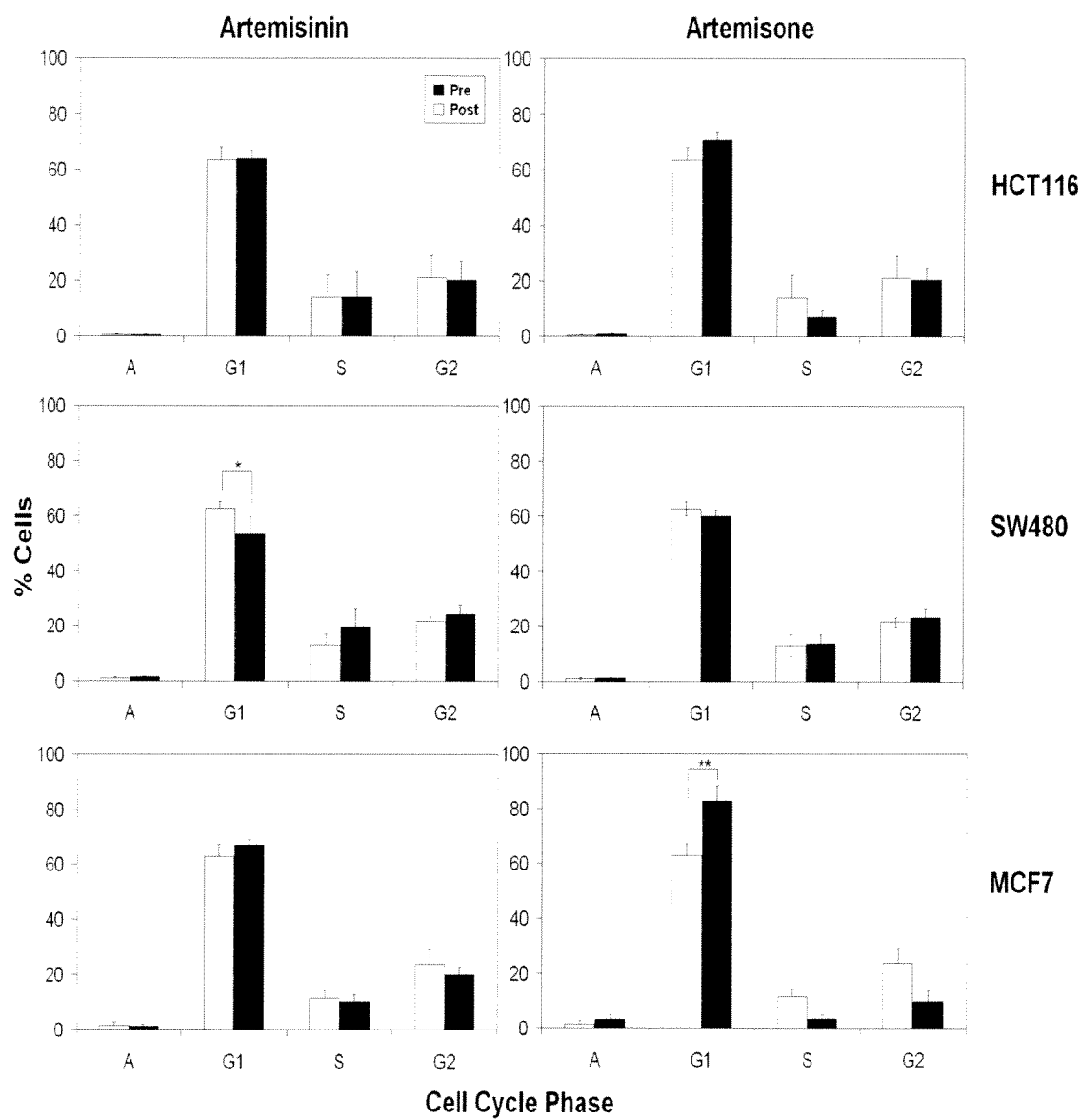

FIG. 2. PI flow cytometric histograms showing the proportion of cells at sub-G1 (apoptotic (A)), G1, S and G2 phases of the cell cycle in response to equi-active concentrations of the ART and ATM in three different cell lines. Graph shows untreated versus treated for three separate experiments. MCF7 cells treated with ATM exhibited a significantly greater proportion of cells in G1. Conversely, significantly smaller percentages of cells within G1 were seen in SW480 cells. *p<0.05, **p=0.015.

FIG. 3A-B. 3A) Effects of ART and ATM on levels of intracellular cycling proteins as viewed by western blot. Cells were untreated or treated with equi-active amounts of the two drugs for 72 hrs before running total cellular protein and probing with appropriate antibody. Representative blots are shown. 3B) Protein bands were quantified using densitometry techniques and then the percentage change in protein level compared to untreated controls was calculated. Graphs show mean protein change of 3 separate experiments. Error bars have been omitted for clarity.

FIG. 4A-D. Combinations were analysed using median effect analysis (4A) or modulating dose model (4B-4D). 4A) Combining oxaliplatin (OXP) with the artemisinins produces differing effects depending on the derivative used. The median effect equation was used to generate CI values which, when above 1 indicate antagonism and below 1 enhancement of effect. 4B) Small doses of gemcitabine (GEM) were used to modulate the IC50 of ART and ATM in different cell lines. IC50 is greatly increased when GEM is added to ART whilst this effect is less prevalent with ATM. 4C) Combination with thalidomide (THAL) did not greatly affect the IC50 of ART or ATM in any of the cell lines. 4D) Lenalidomide (LEN) combination, however, produced a strong enhancement of effect for both compounds in all three cell lines. All values represent a mean and SDs of at least 3 experiments.

Figure 5:
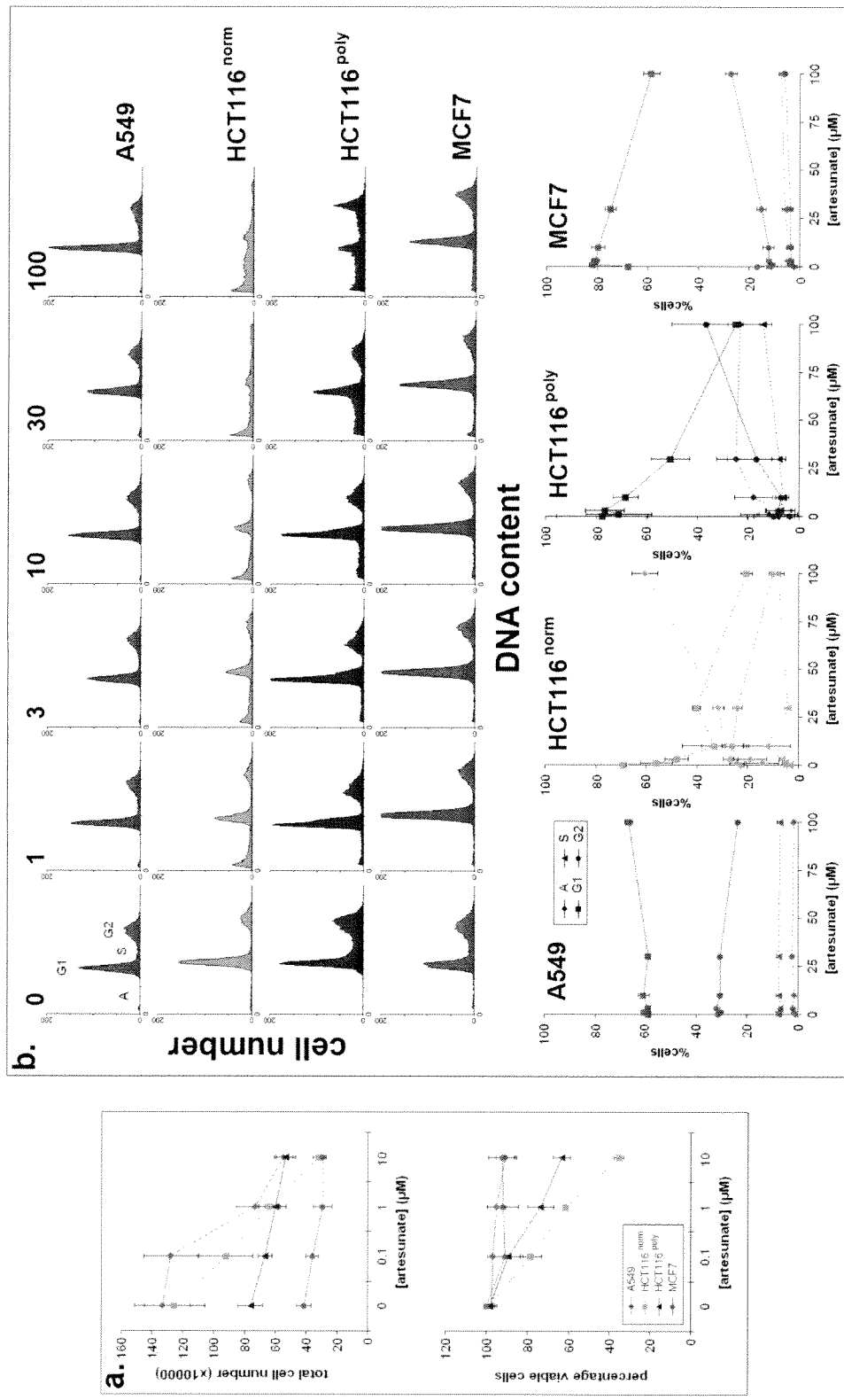

FIG. 5A-B. Effect of Artesunate on cell proliferation and cell cycle dynamics. 5A) A549, HCT116$^{norm}$, HCT116$^{poly}$ and MCF7 cells were cultured with ART (0-100 μM) for 72 hr prior to assessing cell number and viability by cell counting with trypan blue dye discrimination. Each data point is the mean and SDs of three separate experiments. 5B) Cell cycle distribution in sub-G1 (A), G1, S and G2 by propidium iodide staining and flow cytometric analysis of cells. There were significant increases in the sub-G1 population in HCT116$^{norm}$ and HCT116$^{poly}$ cells that indicated cytotoxicity. Conversely, no clear changes to profiles for A549 and MCF7 cells suggested a general global cell cycle arrest. Representative histograms are represented in the upper panel of, and the means and SDs of at least four independent replicates are represented in the lower line graphs.

Figure 6:
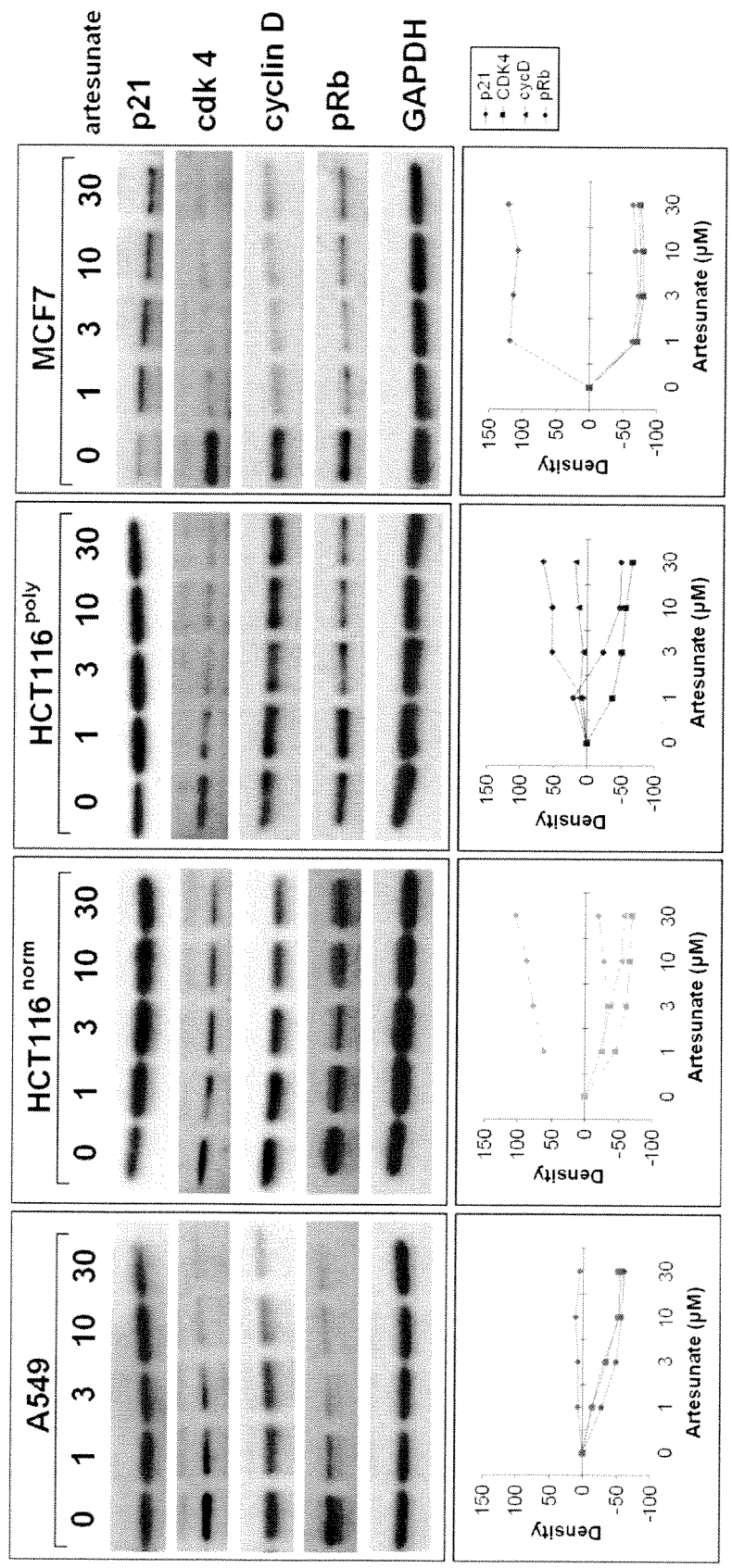

FIG. 6. Effect of Artesunate on proteins that regulate transit through the G1 restriction point. Each of the cell lines were cultured with Artesunate (0-30 μM) for 72 hr before western blotting for the proteins indicated. There were decreased expressions of pRb in all the cell lines, which were associated with reductions in CDK4 and/or cyclinD. These were generally mirrored by increases in p21. Representative blots are shown, and data from densitometric analysis of three independent experiments are shown in the lower line graphs. SDs have been omitted for clarity, but coefficient of variances for most points were <10%.

Figure 7:
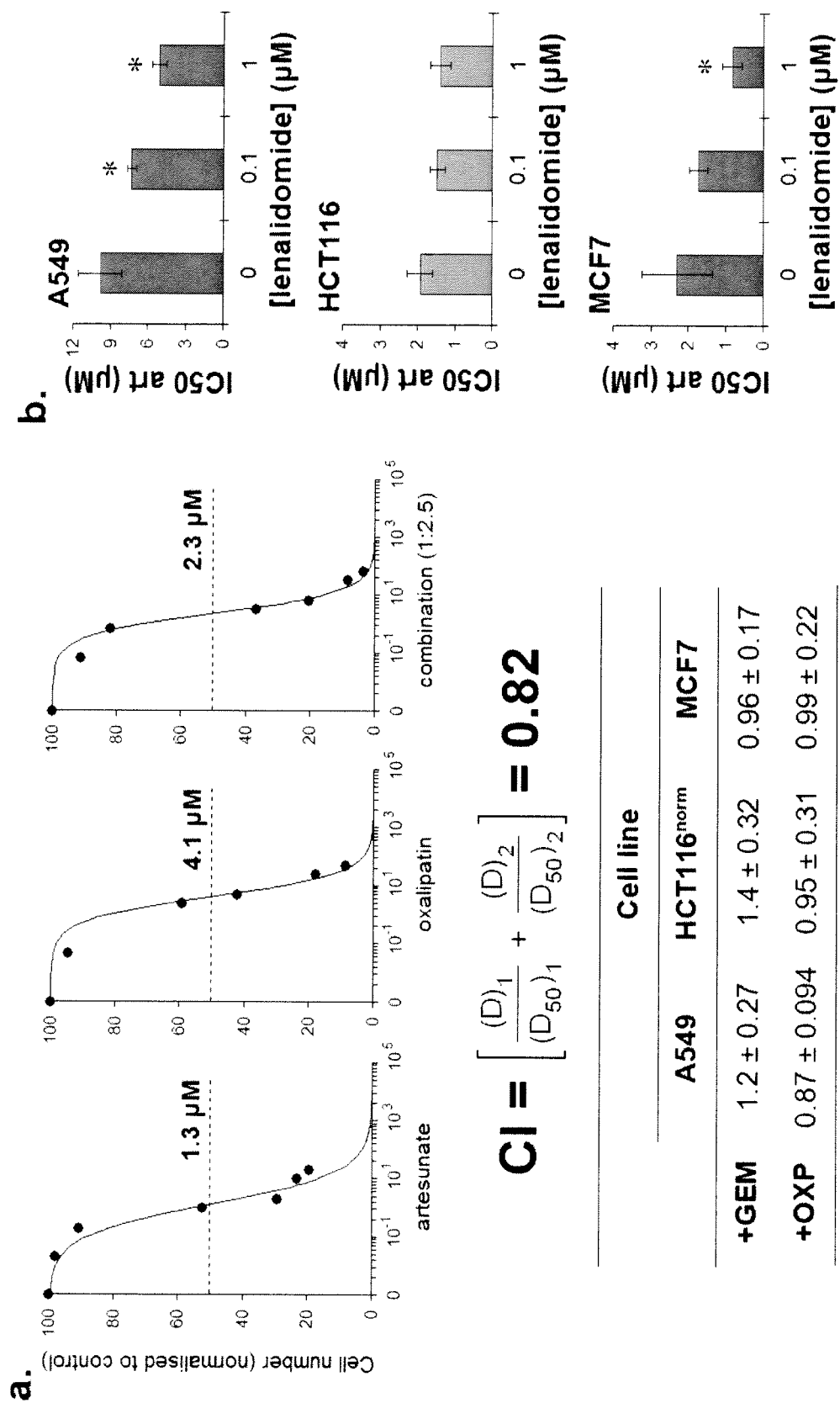

FIG. 7A-B. Effect of combining Artesunate with chemotherapy in A549, HCT116$^{norm}$ and MCF7 cells. 7A) Cells were cultured concomitantly with Artesunate and GEM or Artesunate and OXP for 72 hr. before assessing cell numbers by MTT. Non-exclusive CI values for the 50% unaffected fraction were calculated and shown in the lower panel. CI-values>1 indicates antagonis; CI=1 additivity and CI<1 synergy. Representative response curves and the extrapolated IC50-values for Artesunate, OXP and a combination of the two drugs (combined at equi-molar fractions of respective IC50 values, which was at a ratio of 1:2.5) are shown in the upper panel. 7B) Cells were cultured with a range of Artesunate in the absence or presence of small non-growth inhibitory concentrations of LEN (0.1 and 1 μM), to assess the effects of these doses on the responses of the cells to Artesunate. There were significant enhancements of Artesunate activity as indicated by reductions in the IC50s for Artesunate when used in the presence of LEN in A549 and MCF7 cells. Each point is the mean and SDs of at least three independent experiments, and the asterices indicate significant difference compared to the LEN-free culture (p<0.001).

FIG. 8A-D. Effect of Artesunate on HCT116$^{poly}$ cells. 8A-B) HCT116$^{norm}$ cells were over-passaged for 10-12 weeks, and the ploidy of these cells (HCT116$^{poly}$) assessed by using propidium iodide staining and flow cytometry. The percentage of hyperploid cells was increased over the parental HCT116$^{norm}$, as indicated by increases in the number of cells with a high FL3-A expression but similar FL3-W values. Additionally, distinct hyperploidy populations were observed in the FL3-H channel. 8C) Culturing with Artesunate resulted in a G2-blockade and a modest increase in the sub-G1 (n<2) in HCT116$^{poly}$ cells. 8D) In HCT116$^{norm}$ cells there was no blockade, rather a more pronounced increase in the dying population. Western blotting data revealed differences in cyclin B and BAX proteins in response to Artesunate. Artesunate was associated with a decrease in cyclin B in HCT116$^{norm}$ cells, but an increase in HCT116$^{poly}$ cells. Similarly, having seen no effect on BAX in HCT116$^{norm}$, Artesunate caused a decrease in BAX expression in HC116$^{poly}$. Each data point is the mean and SD of at least three separate experiments. Autoradiograms and representative of three independent experiments, and densitometry results are the mean data for each band normalised to its respective GAPDH loading control. Error bars have been omitted for space.

FIG. 9A-D. Effect of a drug-free period in an Artesunate treatment schedule. 9A) HCT116$^{poly}$ cells were cultured with 30 μM Artesunate for 2-days before removal of drug. Cells were then returned to fresh culture medium supplemented with or without 30 μM ART. Cell viability and cell cycle distribution were then assessed on day 4. Results showed that culturing cells with Artesunate for 2-days prior to returning them to drug-free medium significantly decreased cell viability, compared to culturing cells with ART for the entire 4-days. 9B) Similar treatment schedules were also tested in A549 and MCF7 cells, where each column signifies the cell viability on day 0, 2 or 4. Each of the columns represents the mean and SD of at least 3 separate experiments. Representative Flow cytometric histograms from three separate experiments are shown in (a), and include the mean percentage of cells within the sub-G1 or G2 phase.

5. DETAILED DESCRIPTION

5.1 Compounds
5.1.1 Immunomodulatory Compounds

Any suitable immunomodulatory compounds can be used in the combination therapy methods described herein. Exemplary immunomodulatory compounds that can be administered include but are not limited to N-{[2-(2,6-dioxo(3-piperidyl)-1,3-dioxoisoindolin-4-yl]methyl}cyclopropyl-carboxamide; 3-[2-(2,6-dioxo-piperidin-3-yl)-1,3-dioxo-2,3-dihydro-1H-isoindol-4-ylmethyl]-1,1-dimethyl-urea; (−)-3-(3,4-Dimethoxy-phenyl)-3-(1-oxo-1,3-dihydro-isoindol-2-yl)-propionamide; (+)-3-(3,4-Dimethoxy-phenyl)-3-(1-oxo-1,3-dihydro-isoindol-2-yl)-propionamide; (−)-{2-[1-(3-ethoxy-4-methoxyphenyl)-2-methylsulfonylethyl]-4-acetylaminoisoindoline-1,3-dione}; (+)-{2-[1-(3-ethoxy-4-methoxyphenyl)-2-methyl sulfonylethyl]-4-acetylaminoisoindoline-1,3-dione}; Difluoro-methoxy SelCIDs; 1-phthalimido-1-(3,4-diethoxyphenyl)ethane; 3-(3,4-dimethoxyphenyl)-3-(3,5-dimethoxyphenyl)acrylonitrile; 1-oxo-2-(2,6-dioxopiperidin-3-yl)-4-aminoisoindoline; 1,3-dioxo-2-(2,6-dioxopiperidin-3-yl)-4-aminoisoindoline; 4-amino-2-(3-methyl-2,6-dioxo-piperidine-3-yl)-isoindole-1,3-dione; 3-(3-acetoamidophthalimido)-3-(3-ethoxy-4-methoxyphenyl)-N-hydroxypropionamide; 1-oxo-2-(2,6-dioxopiperidin-3-yl)-4-methylisoindoline; Cyclopropyl-N-{2-[(1S)-1-(3-ethoxy-4-methoxyphenyl)-2-(methylsulfonyl)ethyl]-3-oxoisoindoline-4-yl}carboxamide: Substituted 2-(3-hydroxy-2,6-dioxopiperidin-5-yl) isoindoline: N-[2-(2,6-Dioxo-piperidin-3-yl)-1,3-dioxo-2,3-dihydro-1H-isoindol-5-ylmethyl]-4-trifluoromethoxybenzamide; (S)-4-chloro-N-((2-(3-methyl-2,6-dioxopiperidin-3-yl)-1,3-dioxoisoindolin-5-yl)methyl)benzamide; Pyridine-2-carboxylic acid [2-[(3S)-3-methyl-2,6-dioxo-piperidin-3-yl]-1,3-dioxo-2,3-dihydro-1H-isoindol-5-ylmethyl]-amide: (S)—N-((2-(3-methyl-2,6-dioxopiperidin-3-yl)-1,3-dioxoisoindolin-5-yl)methyl)-4-(trifluoromethyl)benzamide: 3-(2,5-dimethyl-4-oxo-4H-quinazolin-3-yl)-piperidine-2,6-dione, and the like.

Without being limited by theory, immunomodulatory compounds disclosed herein may be potent co-stimulators of T cells and increase cell proliferation dramatically in a dose dependent manner. Immunomodulatory compounds disclosed herein may also have a greater co-stimulatory effect on the $CD8^+$ T cell subset than on the $CD4^+$ T cell subset. In addition, the compounds may have anti-inflammatory properties against myeloid cell responses, yet efficiently co-stimulate T cells to produce greater amounts of IL-2, IFN-γ, and to enhance T cell proliferation and $CD8^+$ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the ability of NK cells to produce beneficial cytokines such as, but not limited to, IFN-γ, and to enhance NK and NKT cell cytotoxic activity.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), substituted 2-(2,6-dioxopiperidin-3-yl) phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239: isoindoline-1-one and isoindoline-1,3-dione substituted in the 2-position with 2,6-dioxo-3-hydroxypiperidin-5-yl (e.g. 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552. U.S. Pat. No. 7,091,353, and International Application No. PCT/US01/50401 (International Publication No. WO 02/059106), patent publication no. 2006/0205787 describes 4-amino-2-(3-methyl-2,6-dioxopiperidin-3-yl)-isoindole-1,3-dione compositions, patent publication no. 2007/0049618 describes isoindole-imide compounds. The entireties of each of the patents and patent applications identified herein are incorporated by reference. In one embodiment, immunomodulatory compounds do not include thalidomide.

Various immunomodulatory compounds disclosed herein contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, 1N, 1972), each of which is incorporated by reference herein in its entirety.

Immunomodulatory compounds provided herein include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference.

These compounds have the structure:

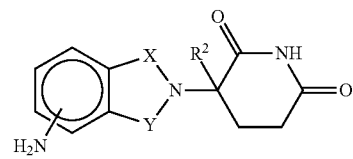

in which one of X and Y is C═O, the other of X and Y is C═O or $CH_2$, and $R^2$ is hydrogen or lower alkyl, in particular methyl. Specific immunomodulatory compounds include, but are not limited to:

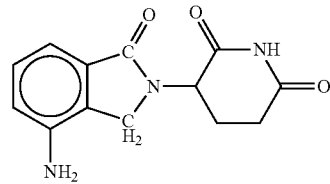

1-oxo-2-(2,6-dioxopiperidin-3-yl)-4-aminoisoindoline (lenalidomide):

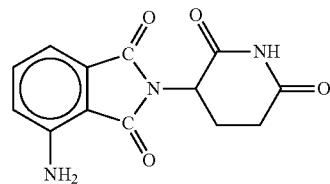

1,3-dioxo-2-(2,6-dioxopiperidin-3-yl)-4-aminoisoindoline (pomalidomide); and

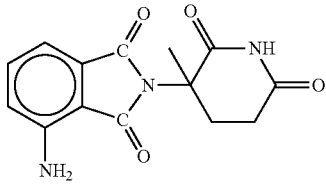

1,3-dioxo-2-(3-methyl-2,6-dioxopiperidin-3-yl)-4-aminoisoindole, and optically pure isomers thereof.

The compounds can be obtained via standard, synthetic methods (see e.g., U.S. Pat. No. 5,635,517, incorporated herein by reference). The compounds are also available from Celgene Corporation, Warren, N.J.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

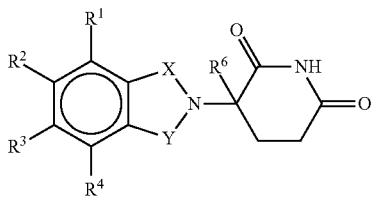

in which:
one of X and Y is C=O and the other of X and Y is C=O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzyl, or halo;
provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.
Compounds representative of this class are of the formulas:

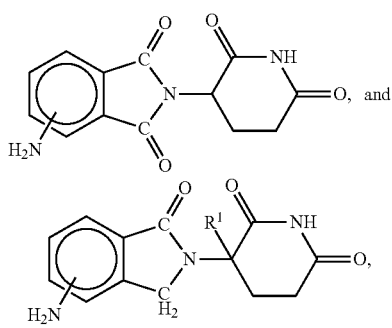

wherein $R^1$ is hydrogen or methyl. In a separate embodiment, the invention encompasses the use of enantiomerically pure forms (e.g. optically pure (R) or (S) enantiomers) of these compounds.

Still other specific immunomodulatory compounds disclosed herein belong to a class of isoindole-imides disclosed in U.S. Pat. No. 7,091,353, U.S. Patent Publication No. 2003/0045552, and International Application No. PCT/US01/50401 (International Publication No. WO 02/059106), each of which are incorporated herein by reference. Representative compounds are of formula:

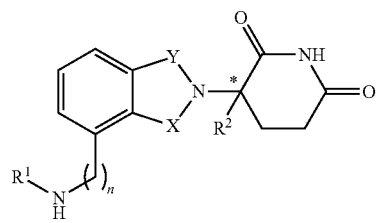

and pharmaceutically acceptable salts, hydrates, solvates, clathrates, enantiomers, diastereomers, racemates, and mixtures of stereoisomers thereof, wherein:
one of X and Y is C=O and the other is $CH_2$ or C=O;
$R^1$ is H, $(C_1$-$C_8)$alkyl, $(C_3$-$C_7)$cycloalkyl, $(C_2$-$C_8)$alkenyl, $(C_2$-$C_8)$alkanyl, benzyl, aryl, $(C_0$-$C_4)$alkyl-$(C_1$-$C_6)$heterocycloalkyl, $(C_0$-$C_4)$alkyl-$(C_2$-$C_5)$heteroaryl, $C(O)R^3$, $C(S)R^3$, $C(O)OR^4$, $(C_1$-$C_8)$alkyl-$N(R^6)_2$, $(C_1$-$C_8)$alkyl-$OR^5$, $(C_1$-$C_8)$alkyl-$C(O)OR^5$, $C(O)NHR^3$, $C(S)NHR^3$, $C(O)NR^3R^{3'}$, $C(S)NR^3R^{3'}$ or $(C_1$-$C_8)$alkyl-$O(CO)R^5$;
$R^2$ is H, F, benzyl, $(C_1$-$C_8)$alkyl, $(C_2$-$C_8)$alkenyl, or $(C_2$-$C_8)$alkynyl;
$R^3$ and $R^{3'}$ are independently $(C_1$-$C_8)$alkyl, $(C_3$-$C_7)$cycloalkyl, $(C_2$-$C_8)$alkenyl, $(C_2$-$C_8)$alkynyl, benzyl, aryl, $(C_0$-$C_4)$alkyl-$(C_1$-$C_6)$heterocycloalkyl, $(C_0$-$C_4)$alkyl-$(C_2$-$C_5)$heteroaryl, $(C_0$-$C_8)$alkyl-$N(R^6)_2$, $(C_1$-$C_8)$alkyl-$OR^5$, $(C_1$-$C_8)$alkyl-$C(O)OR^5$, $(C_1$-$C_8)$alkyl-$O(CO)R^5$, or $C(O)OR^5$;
$R^4$ is $(C_1$-$C_8)$alkyl, $(C_2$-$C_8)$alkenyl, $(C_2$-$C_8)$alkynyl, $(C_1$-$C_4)$alkyl-$OR^5$, benzyl, aryl, $(C_0$-$C_4)$alkyl-$(C_1$-$C_6)$heterocycloalkyl, or $(C_0$-$C_4)$alkyl-$(C_2$-$C_5)$heteroaryl;
$R^5$ is $(C_1$-$C_8)$alkyl, $(C_2$-$C_8)$alkenyl, $(C_2$-$C_8)$alkynyl, benzyl, aryl, or $(C_2$-$C_8)$heteroaryl; each occurrence of $R^6$ is independently H, $(C_1$-$C_8)$alkyl, $(C_2$-$C_8)$alkenyl, $(C_2$-$C_8)$alkynyl, benzyl, aryl, $(C_2$-$C_5)$heteroaryl, or $(C_0$-$C_8)$alkyl-$C(O)O$—$R^5$ or the $R^6$ groups can join to form a heterocycloalkyl group;
n is 00 or 1; and
* represents a chiral-carbon center.

In specific compounds of the formula, when n is 0 then $R^1$ is $(C_3$-$C_7)$cycloalkyl, $(C_2$-$C_8)$alkenyl, $(C_2$-$C_8)$alkynyl, benzyl, aryl, $(C_0$-$C_4)$alkyl-$(C_1$-$C_6)$heterocycloalkyl, $(C_0$-$C_4)$alkyl-$(C_2$-$C_5)$heteroaryl, $C(O)R^3$, $C(O)OR^4$, $(C_1$-$C_8)$alkyl-$N(R^6)_2$, $(C_1$-$C_8)$alkyl-$OR^5$, $(C_1$-$C_8)$alkyl-$C(O)OR^5$, $C(S)NHR^3$, or $(C_1$-$C_8)$alkyl-$O(CO)R^5$;
$R^2$ is H or $(C_1$-$C_8)$alkyl; and
$R^3$ is $(C_1$-$C_8)$alkyl, $(C_3$-$C_7)$cycloalkyl, $(C_2$-$C_8)$alkenyl, $(C_2$-$C_8)$alkynyl, benzyl, aryl, $(C_0$-$C_4)$alkyl-$(C_1$-$C_6)$heterocycloalkyl, $(C_0$-$C_4)$alkyl-$(C_2$-$C_8)$heteroaryl, $(C_5$-$C_8)$alkyl-$N(R^6)_2$; $(C_0$-$C_8)$alkyl-$NH$—$C(O)O$—R; $(C_1$-$C_8)$alkyl-$OR^5$, $(C_1$-$C_8)$alkyl-$C(O)ORS$, $(C_1$-$C_8)$alkyl-$O(CO)R^5$, or $C(O)OR^5$; and the other variables have the same definitions.

In other specific compounds of formula II, $R^2$ is H or $(C_1$-$C_4)$alkyl.

In other specific compounds of formula II, $R^1$ is $(C_1$-$C_8)$ alkyl or benzyl.

In other specific compounds of formula II, $R^1$ is H, $(C_1-C_8)$alkyl, benzyl, $CH_2OCH_3$, $CH_2CH_2OCH_3$, or

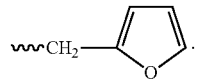

In another embodiment of the compounds of formula II. $R^1$ is

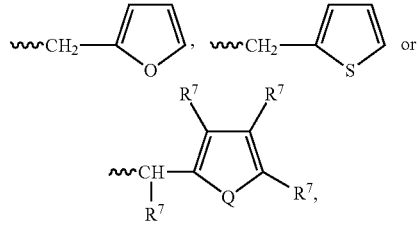

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$ heterocycloalkyl, $(C_0-C_4)$alkyl-$(C_2-C_5)$heteroaryl, $(C_0-C_8)$ alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula II. $R^3$ is $(C_0-C_4)$ alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O) NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl)}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; {N-(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide: N-(2-(2,6-dioxo(3-piperidyl))-1,3-dioxoisoindolin-4-yl)-2-thienylcarboxamide: N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl] methyl}(octylamino)carboxamide: and N-{[2-(2,6-dioxo(3-piperidyl))-1,3-dioxoisoindolin-4-yl]methyl}(benzylamino) carboxamide.

Still other specific immunomodulatory compounds disclosed herein belong to a class of isoindole-imides disclosed in U.S. Pat. No. 6,555,554, International Publication No. WO 98/54170, and U.S. Pat. No. 6,395,754, each of which is incorporated herein by reference. Representative compounds are of formula:

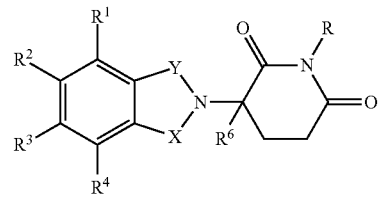

and pharmaceutically acceptable salts, hydrates, solvates, clathrates, enantiomers, diastereomers, racemates, and mixtures of stereoisomers thereof, wherein:
one of X and Y is C=O and the other is $CH_2$ or C=O;
R is H or $CH_2OCOR'$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;
$R^5$ is hydrogen or alkyl of 1 to 8 carbons
$R^6$ hydrogen, alkyl of 1 to 8 carbon atoms, benzo, chloro, or fluoro;
R' is $R^7$—$CHR^{10}$—$N(R^8R^9)$;
$R^7$ is m-phenylene or p-phenylene or —$(CnH2n)$- in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2C_2$— in which $X^1$ is —O—, —S—, or —NH—;
$R^{10}$ is hydrogen, alkyl of to 8 carbon atoms, or phenyl; and
* represents a chiral-carbon center.
Other representative compounds are of formula:

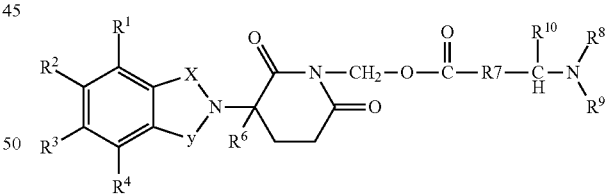

wherein:
one of X and Y is C=O and the other of X and Y is C=O or $CH_2$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzo, chloro, or fluoro;
$R^7$ is m-phenylene or p-phenylene or —$(CnH2n)$- in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —CH$_2$CH$_2$X$^1$CH$_2$CH$_2$— in which X$^1$ is —O—, —S—, or —NH—; and R$^{10}$ is hydrogen, alkyl of to 8 carbon atoms, or phenyl.

Other representative compounds are of formula:

in which
one of X and Y is C=O and the other of X and Y is C=O or CH$_2$;
each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is nitro or protected amino and the remaining of R$^1$, R$^2$, R$^3$ and R$^4$ are hydrogen; and
R$^6$ is hydrogen, alkyl of 1 to 8 carbon atoms, benzo, chloro, or fluoro.

Other representative compounds are of formula:

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen, alkyl of 1 to 8 carbon atoms, or CO—R$^7$—CH(R$^{10}$)NR$^8$R in which each of R$^7$, R$^8$, R$^9$, and R$^{10}$ is as herein defined; and
R$^6$ is alkyl of 1 to 8 carbon atoms, benzo, chloro, or fluoro.

Specific examples of the compounds are of formula:

in which:
one of X and Y is C=O and the other of X and Y is C=O or CH$_2$;
R$^6$ is hydrogen, alkyl of 1 to 8 carbon atoms, benzyl, chloro, or fluoro;
R$^7$ is m-phenylene, p-phenylene or —(CnH2n)- in which n has a value of 0 to 4; each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and R$^{10}$ is hydrogen, alkyl of 1 to 8 carbon atoms, or phenyl.

Other specific immunomodulatory compounds are 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

wherein:
Y is oxygen or H$_2$ and
each of R$^1$, R$^2$, R$^3$, and R$^4$, independently of the others, is hydrogen, halo, alkyl of 1 to 4 carbon atoms, alkoxy of 1 to 4 carbon atoms, or amino.

Other specific immunomodulatory compounds are the tetra substituted 2-(2,6-dioxopiperidin-3-yl)-1-oxoisoindolines described in U.S. Pat. No. 5,798,368, which is incorporated herein by reference. Representative compounds are of formula:

wherein each of R$^1$, R$^2$, R$^3$, and R$^4$, independently of the others, is halo, alkyl of 1 to 4 carbon atoms, or alkoxy of 1 to 4 carbon atoms.

Other specific immunomodulatory compounds are 1-oxo and 1,3-dioxo-2-(2,6-dioxopiperidin-3-yl) isoindolines disclosed in U.S. Pat. No. 6,403,613, which is incorporated herein by reference. Representative compounds are of formula:

in which
Y is oxygen or H$_2$,
a first of R$^1$ and R$^2$ is halo, alkyl, alkoxy, alkylamino, dialkylamino, cyano, or carbamoyl, the second of R$^1$ and R$^2$, independently of the first, is hydrogen, halo, alkyl, alkoxy, alkylamino, dialkylamino, cyano, or carbamoyl, and
R$^3$ is hydrogen, alkyl, or benzyl.

Specific examples of the compounds are of formula:

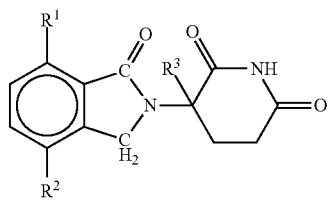

wherein
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;
the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

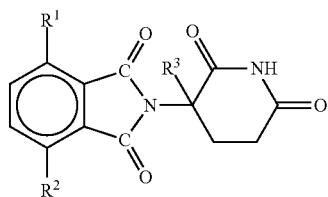

wherein:
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl;
the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl.

Other specific immunomodulatory compounds disclosed herein are 1-oxo and 1,3-dioxoisoindolines substituted in the 4- or 5-position of the indoline ring described in U.S. Pat. No. 6,380,239 and U.S. Pat. No. 7,244,759, both of which are incorporated herein by reference. Representative compounds are of formula:

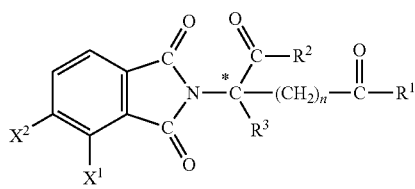

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z: $R^3$ is hydrogen, alkyl of one to six carbons, halo, or haloalkyl; Z is hydrogen, aryl, alkyl of one to six carbons, formyl, or acyl of one to six carbons: and n has a value of 0.1, or 2: provided that if $X^1$ is amino, and n is 1 or 2, then $R^1$ and $R^2$ are not both hydroxy: and the salts thereof.

Further representative compounds are of formula:

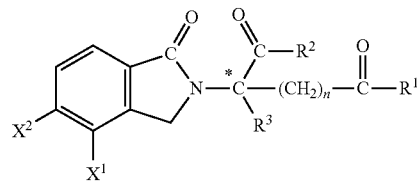

in which the carbon atom designated C* constitutes a center of chirality when n is not zero and $R^1$ is not $R^2$; one of X and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-carbamoyl-butyric acid, which have the following structures, respectively, and pharmaceutically acceptable salts, solvates, prodrugs, and stereoisomers thereof:

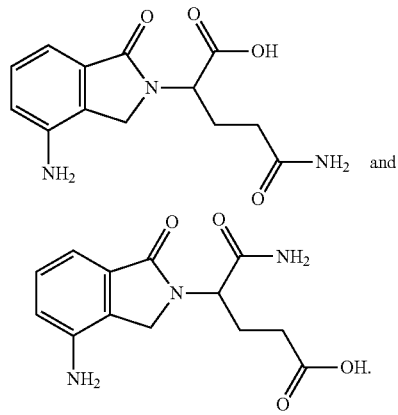

Other representative compounds are of formula:

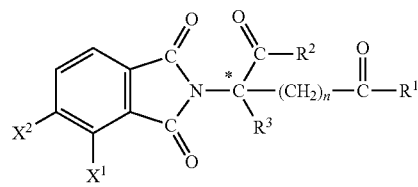

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of X¹ or X² is hydrogen; each of R¹ and R² independent of the other, is hydroxy or NH—Z; R³ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

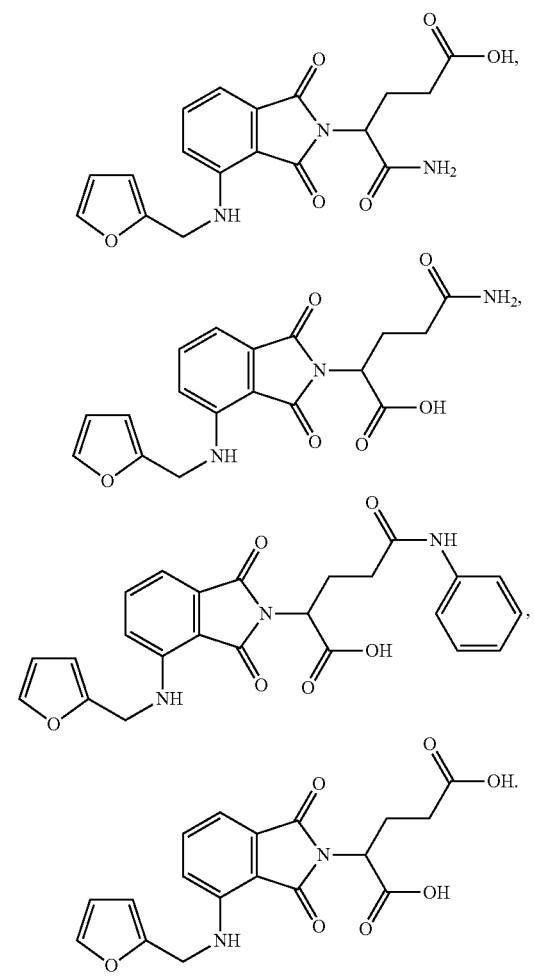

Other specific examples of the compounds are of formula:

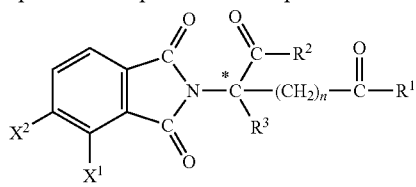

wherein:
one of X¹ and X² is nitro, or NH—Z, and the other of X¹ or X² is hydrogen;

each of R¹ and R², independent of the other, is hydroxy or NH—Z;
R³ is alkyl of one to six carbons, halo, or hydrogen;
Z is hydrogen, phenyl, an acyl of one to six carbons, or an alkyl of one to six carbons; and
n has a value of 0, 1, or 2; and
if —COR² and —(CH₂)ₙCOR¹ are different, the carbon atom designated C* constitutes a center of chirality.

Other representative compounds are of formula:

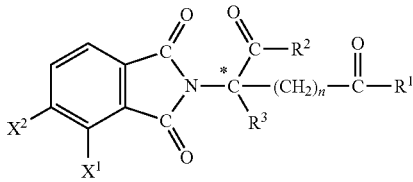

wherein:
one of X¹ and X² is alkyl of one to six carbons;
each of R¹ and R², independent of the other, is hydroxy or NH—Z:
R³ is alkyl of one to six carbons, halo, or hydrogen:
Z is hydrogen, phenyl, an acyl of one to six carbons, or an alkyl of one to six carbons; and
n has a value of 0, 1, or 2; and
if —COR² and —(CH₂)ₙCOR¹ are different, the carbon atom designated C* constitutes a center of chirality.

Still other specific immunomodulatory compounds are isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

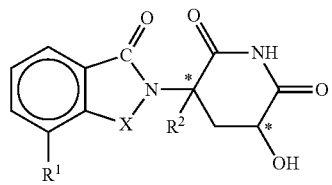

wherein:
the carbon atoms designated * constitute centers of chirality;
X is —C(O)— or —CH₂—;
R¹ is alkyl of 1 to 8 carbon atoms or —NHR³;
R² is hydrogen, alkyl of 1 to 8 carbon atoms, or halogen; and
R³ is hydrogen,
alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —COR⁴ in which
R⁴ is hydrogen,
alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques. Additional information on immunomodulatory compounds, their preparation, and use can be found, for example, in U.S. Patent Application Publication Nos. US20060188475, US20060205787, and US20070049618, each of which is incorporated by reference herein in its entirety.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2 Methods of Treatment

5.2.1 Cancer

Many types of cancer can be treated using the combinations of immunomodulatory compounds plus other compounds as disclosed herein. Specific examples of cancer include, but are not limited to: cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. Methods provided herein can also be used to follow the treatment of cancers of the blood and bone marrow, such as multiple myeloma and acute and chronic leukemias, for example, lymphoblastic, myelogenous, lymphocytic, and myelocytic leukemias. The methods provided herein can be used for managing either primary or metastatic tumors.

In some embodiments, the cancer to be treated is multiple myeloma. In other embodiments, the cancer to be treated is not multiple myeloma.

Other specific cancers include, but are not limited to advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, ovarian cancer, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, leiomyoma, and the like. In a specific embodiment, the cancer is metastatic. In another embodiment, the cancer is refractory or resistant to chemotherapy or radiation.

In some embodiments, the cancer is a solid or hematological cancer. Examples include, but are not limited to: ovarian cancer, prostate cancer, pancreatic cancer, leukemias including, but not limited to, chronic lymphocytic leukemia, chronic myelocytic leukemia, acute lymphoblastic leukemia (ALL), acute myelogenous leukemia (AML) and acute myeloblastic leukemia; lymphomas including, but are not limited to, Hodgkin's and non-Hodgkin's lymphomas, including all of the subtypes thereof, and myelomas including, but not limited to, multiple myeloma. In some embodiments, the hematological cancer is multiple myeloma.

Exemplary types of leukemia include, but are not limited to chronic lymphocytic leukemia (CLL), acute lymphoblastic leukemia (ALL), prolymphocytic leukemia (PLL), hairy cell leukemia, and small lymphocytic leukemia (SLL).

Exemplary types of lymphoma include but are not limited to Mantle cell lymphoma, splenic lymphoma, hodgkin's lymphoma, mucosal associated lymphoid tissue lymphoma, diffuse small lymphocytic lymphoma, follicular lymphoma, mocytoid B cell lymphoma, Burkitt's lymphoma, AIDS-related lymphoma, diffuse large B-cell lymphoma, lymphomatoid granulomatosis, intravascular lymphomatosis, intravascular lymphoma, cutaneous B-cell lymphoma, and non-hodgkins lymphoma.

5.2.2 Methods of Administration

Methods provided herein comprise administering one or more immunomodulatory compounds, or a pharmaceutically acceptable salt, solvate, stereoisomer, or prodrug thereof, in combination with an artemisinin or a derivative thereof to a patient (e.g., a human) suffering, or likely to suffer, from a cancer-related disease or disorder.

Any of the components of the composition can be administered together or separately. Each of the components can be administered by any suitable means. In some embodiments, at least a part of the formulation is administered using intravenous administration. In some embodiments, intravenous administration can occur by infusion over a period of about less than 1 hour to about 10 hours (less than 1, 2, 3, 4, 5, 6, 7, 8, 9, or 10 hours). Subsequent infusions can be administered over a period of about less than 1 to about 6 hours or more, including, for example, about 1 to about 4 hours, about 1 to about 3 hours, or about 1 to about 2 hours or less than an hour. Alternatively, a dose can be administered subcutaneously or by other means.

In some embodiments, at least a part of the formulation is administered orally. Pharmaceutical compositions that are suitable for oral administration can be presented as in several types of forms, such as, but not limited to, tablets, caplets, capsules, and liquids. In some embodiments, oral administration of a component of the composition can occur prior to, after, or during the administration of the other components. For example, oral administration of at least one of the components can occur 2 weeks, 1 week, 3 days, one day, 12 hours, 1 hour, or 30 minutes prior to or after administration of the other components of the composition. Oral administration of at least one component of the composition can occur several times per day, daily, once every other day, once weekly, and the like.

In preferred embodiments, a daily dose of lenalidomide to be administered can be in the range from about 5 mg per day to about 25 mg per day. A single dose of the immunomodulatory compound to be administered can be, for example, in the range from about 0.1 mg/kg of patient body weight to about 300 mg/kg, from about 0.1 mg/kg to about 200 mg/kg, from about 0.1 mg/kg to about 50 mg/kg, from about 0.5 mg/kg to about 200 mg/kg, from about 1 mg/kg to about 150 mg/kg, from about 3 mg/kg to about 300 mg/kg, from about 3 mg/kg to about 200 mg/kg, from about 5 mg/kg to about 100 mg/kg, from about 10 mg/kg to about 50 mg/kg.

Thus, for example, the immunomodulatory compound dose can be 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 50 mg/kg, 75 mg/kg, 100 mg/kg, 150 mg/kg, 200 mg/kg, 250 mg/kg, 300 mg/kg, or other such doses falling within the range of about 0.1 mg/kg to about 300 mg/kg.

Similarly, a single dose of the artemisinin or a derivative thereof to be administered can be, for example, in the range from about 0.1 mg/kg to about 100 mg/kg, from about 0.1 mg/kg to about 75 mg/kg, from about 0.1 mg/kg to about 50 mg/kg, from about 0.5 mg/kg to about 50 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg.

Thus, for example, the artemisinin or derivative thereof can be 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, mg/kg, 15 mg/kg, 20 mg/kg, 25 mg/kg, 30 mg/kg, 40 mg/kg, 50 mg/kg, 75 mg/kg, 100 mg/kg, or other such doses falling within the range of about 0.1 mg/kg to about 100 mg/kg.

Administration of the immunomodulatory compound "in combination with" one or more further therapeutic agents includes simultaneous (concurrent) and consecutive administration in any order. Thus, the immunomodulatory compound can be administered at the same time, or prior to, or after one or more of the compounds in the combination. For example, the composition to be administered can contain all of the ingredients in the combination. Alternatively, one or more of the compounds in the composition can be administered before or after the other compounds. In one embodiment, the immunomodulatory compound can be administered at the same time as the other components in the composition. In another embodiment, the immunomodulatory compound can be administered from about 0, 10, 30, to about 60 minutes or more after administration of at least one of the other compounds in the composition. In other embodiments, the immunomodulatory compound can be administered from about 1, 6, 12, or 24 hours to about 2 days, 4 days, 1 week, or about 2 weeks after administration of at least one of the other compounds in the composition.

In some embodiments, it is advantageous to pretreat the patient with the immunomodulatory compound prior to administration of a second compound, particularly so that cellular changes (such as protein expression) effected by the immunomodulatory compound can already be present when the second compound is administered. In an embodiment, the immunomodulatory compound can be administered from about 0, 10, 30, to about 60 minutes before administration of an artemisinin or a derivative thereof. In another embodiment, the immunomodulatory compound can be administered from about 1, 6, 12, or 24 hours to about 2 days, 4 days, 1 week, or about 2 weeks before administration of an artemisinin or a derivative thereof.

The immunomodulatory compound can be administered by the same route, or by a different route, than the other compound or compounds in the combination. For example, some of the components of the composition can be administered orally, while others are administered intravenously. In additional embodiments, some of the components are administered by subcutaneous injection, while other components are administered by infusion.

5.3 Pharmaceutical Compositions and Dosage Forms

The composition of an immunomodulatory compound in combination with an artemisinin or a derivative thereof can be formulated into desired dosage forms. For example, single or multiple unit dosage forms can be prepared.

The compositions can be formulated to be suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a cancer-related disease or disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same cancer-related disease or disorder. These and other ways in which specific dosage forms encompassed by this invention will vary from one another will be readily apparent to those skilled in the art. (See, e.g., *Remington's Pharmaceutical Sciences,* 18th ed., Mack Publishing, Easton Pa. (1990)).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients, or when exposed to water.

Further provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. (See, e.g., Jens T. Carstensen, *Drug Stability: Principles & Practice,* 2d. Ed., Marcel Dekker, NY, N.Y., 1995, pp. 379-80, which is incorporated by reference herein in its entirety). In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, in some embodiments, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, strip packs, and the like.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, salt buffers, and the like.

The amounts and specific types of active ingredients in a dosage form may differ depending on factors such as, but not limited to, the route by which it is to be administered to patients. Thus, in some embodiments, typical dosage forms comprise an immunomodulatory compound or a pharmaceutically acceptable salt, solvate, stereoisomer, or prodrug thereof in an amount of from about 1 mg to about 250 mg. In some embodiments, dosage forms can comprise an immunomodulatory compound or a pharmaceutically acceptable salt, solvate, stereoisomer, or prodrug thereof in an amount of about 2, 5, 7.5, 10, 12.5, 15, 17.5, 20, 25, 50, 100, 150 or 200 mg. Typical dosage forms comprise the second active ingredient, such as an artemisinin or a derivative thereof, in an amount of from about 0.1 to about 1000 mg, from about 5 to about 500 mg, from about 10 to about 350 mg, or from about 50 to about 200 mg. The specific amount of the agent will depend on the specific agent used, the type of cancer-related disease or disorder being treated or managed, and the amount(s) of an immunomodulatory compound and any optional additional active agents concurrently administered to the patient.

5.3.1 Parenteral Dosage Forms

Parenteral dosage forms can be administered to patients by various routes including, but not limited to, subcutaneous, intravenous (including bolus injection), intramuscular, intraarterial, and the like. Parenteral administration typically bypasses an individual's natural defenses against contaminants, so these dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, emulsions, and the like.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, benzyl benzoate, and the like.

Compounds that increase the solubility of one or more of the active ingredients disclosed herein can also be incorporated into parenteral dosage forms. For example, cyclodextrin and its derivatives can be used to increase the solubility of an immunomodulatory compound and its derivatives. (See, e.g., U.S. Pat. No. 5,134,127, which is incorporated herein by reference).

5.3.2 Oral Dosage Forms

One or more of the components of the composition can be administered orally, if desired. Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms can be prepared by combining the active ingredients with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, coloring agents, and the like. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, disintegrating agents, and the like.

If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, lubricants, and the like. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, mixtures thereof, and the like.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, mixtures thereof, and the like. The binder or filler in pharmaceutical compositions is typically present in from about 50 to about 99 weight percent of the pharmaceutical composition or dosage form.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, mixtures thereof, and the like.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, mixtures thereof, and the like.

5.3.3 Delayed Release Dosage Forms

One or more of the active components of the combination composition can be administered by a delayed release means, if desired. Controlled release means or by delivery devices are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients. Also provided herein are single unit dosage forms suitable for oral administration such as, but not limited to, tablets, capsules, gelcaps, and caplets that are adapted for controlled-release.

Among the advantages of controlled-release formulations are the extended activity of the drug, reduced dosage frequency, and increased patient compliance. In addition, controlled-release formulations can be used to affect the time of onset of action or other characteristics, such as blood levels of the drug, and can thus affect the occurrence of side effects.

Most controlled-release formulations are designed to initially release an amount of the active ingredient that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.3.4 Topical and Mucosal Dosage Forms

In some embodiments, at least one of the components of the combination formulation can be administered topically or mucosally. Topical and mucosal dosage forms include, but are not limited to, sprays, aerosols, solutions, emulsions, suspensions, eye drops or other ophthalmic preparations, or other forms known to one of skill in the art. (See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985)). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms are well known to those skilled in the pharmaceutical arts, and depend on the particular tissue to which a given pharmaceutical composition or dosage form will be applied. Typical excipients include, but are not limited to, water, acetone, ethanol, ethylene glycol, propylene glycol, butane-1,3-diol, isopropyl myristate, isopropyl palmitate, mineral oil, mixtures thereof, and the like. The excipients can form solutions, emulsions or gels, which are non-toxic and pharmaceutically acceptable. Moisturizers or humectants can also be added to pharmaceutical compositions and dosage forms if desired. Examples of such additional ingredients are well known in the art. (See, e.g., *Remington's Pharmaceutical Sciences,* 16th and 18th eds., Mack Publishing, Easton Pa. (1980 & 1990)).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Various salts, hydrates or solvates of the active ingredients can be used to further adjust the properties of the resulting composition.

5.3.5 Kits

In some embodiments, a kit for treating cancer is provided. A typical kit comprises the combination of a dosage form of an immunomodulatory compound, or a pharmaceutically acceptable salt, solvate, stereoisomer, or prodrug thereof, an artemisinin or a derivative thereof. Kits can further comprise additional active and inactive ingredients.

Kits can further comprise devices that are used to administer the active ingredients. Examples of such devices include, but are not limited to, syringes, drip bags, patches, inhalers, and the like. Kits can also contain instruction sheets for use. The kits can be for single use, or can be designed for multiple dosage use.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to ethyl alcohol, polyethylene glycol and polypropylene glycol: and non-aqueous vehicles such as, but not limited to, corn oil, cottonseed oil, peanut oil, sesame oil, ethyl oleate, isopropyl myristate, benzyl benzoate, and the like.

The following examples are offered for illustrative purposes only, and are not intended to limit the scope of the present invention in any way.

6. EXAMPLES

6.1 Anti-Proliferative Effects of Artemisone (ATM)

This example describes the anti-proliferative effect of artemisone (ATM), a novel derivative of artemisinin (ART) in a panel of human cancer cell lines in vitro. The anti-proliferative effects were compared to the parental artemisinin. Additionally, the possible benefits of combining ART derivatives (ARTds) with conventional chemotherapies were also investigated.

In particular, the anti-proliferative effects of ART and ATM were tested on a panel of human cancer cells in vitro, using the methylthiazoletetrazolium assay, and the effect on cell cycling established by flow cytometry. Immunoblot analyses were performed to determine effects at the molecular level. Finally, ART and ATM were combined with common anticancer agents oxaliplatin, gemcitabine, thalidomide and lenalidomide.

6.1.1 Methods

Drugs.

Antimalarial drugs ART and ATM were a kind gift from Professor S. Krishna (St George's University of London, UK) and reconstituted at 10 mM or 50 mM in dimethyl sulphoxide (DMSO) and stored at −20° C. Gemcitabine (GEM: Eli Lilly, Pharmacy, St George's Hospital, UK), oxaliplatin (OXP: Sigma), thalidomide (THA: Celgene Corp., Summit, N.J., USA) and lenalidomide (LEN: Celgene) were all reconstituted in phosphate buffered saline (PBS) and stored at −20° C.

Cell Culture.

The human cancer cell lines; MCF7 (breast), HCT116 and SW480 (colon) (Cancer Research UK, London, UK), KM and MJT3 (melanoma) (in house), PANC1 and MIAPaCa (pancreas) (European Collection of Cell Cultures, Salisbury, UK) were grown in either DMEM (Sigma) or RPMI (Sigma) media supplemented with 10% foetal bovine serum, 2 mM L-glutamine, 1% penicillin/streptomycin. All cell lines were incubated in a humidified atmosphere with 5% $CO_2$ in air at 37° C., and only cells with a passage number <10 were used in the experiments.

Proliferation Assays.

To study the effect of ATM and ART on cell growth, cells growing exponentially were added to 96-well plates at a density of $3 \times 10^4$/well. Drugs (0.1-100 μM) were then added to the wells, ensuring an equal volume of 200 μL across the plate. Cell number/proliferation was measured at 72 hr using a standard methylthiazoletetrazolium (MTT)-based assay without modifications. Briefly, MTT (Sigma) was added to each well to give a working concentration of 0.4 mg/ml, and plates returned to the incubator for a further 1 hr. After this time, the medium was aspirated off, 200 μL of DMSO was then added to each well, and plates agitated gently for 5 min before measuring optical density at 540 nm in each well.

Flow Cytometric Analysis of the Cell Cycle.

Cells were cultured with equi-active concentrations (~IC25) of ART or ATM for 72 hrs, before fixing in 70% (v/v) ethanol in PBS. Following an incubation period of at least 30 mins, cells were washed and re-suspended in a DNA staining solution (1 mg/mL propidium iodide and 1 ng/mL RNAse A (both Sigma). Acquisition of data was performed within 1 h using a Becton Dickinson FACSCalibur (BD Biosciences), and gating was employed to remove doublet artefacts and to discriminate cells from debris. Ten thousand cells were analysed, and the percentages of cells in G1, S and G2/M phases were determined using the cell cycle analysis program WinMDI CellQuest v2.9 (http://facs.scripps.edu/software.html).

Immunoblotting Analysis.

Cells were harvested and total cellular protein was solubilised in lysis buffer (New England Biolabs, Hitchin, UK) and resolved by Tris-glycine electrophoresis using a 4-12% bistris gradient-gel according to the method of Laemmli (Laemmli UK. 1970. Nature, 227(5259):680-5). Following transfer of proteins to nitrocellulose membranes (0.45 μm), blocking was performed in 5% (w/v) non-fat milk in TTBS [0.5% (v/v) Tween-20 in TBS (50 mM Tris, 150 mM NaCl, pH 8.0)]. Primary antibody probing was performed with anti-p53, anti-p21, anti-Bax, anti-CDK4, anti-cyclin D1 or anti-pRb. All primary antibodies were obtained from New England Biolabs (Hitchin, UK) and used at a dilution of 1:1,000, unless stated otherwise. Anti-GAPDH was used as a loading control (1:2, 000—New England). Following five washing steps in TTBS, horseradish peroxidase-conjugated anti-species IgG1 was used as the secondary antibody (Amersham Biosciences Ltd., Little Chalfont, UK). Bands were visualised by the ECL-plus detection system (Amersham).

Combination Studies: Fixing the Ratio of the Concentration of the Drugs.

This combination studies followed an approach previously described (Liu et al. 2008, Leuk Lymphoma, 49(9):1800-9). HCT116, SW480 and MCF7 cells ($5 \times 10^4$/well) growing exponentially were reset in fresh culture medium and aliquoted into 96-well plates. ATM or ART was combined with OXP at an equal ratio of their respective IC50 (eg. ½×IC50 of ART was combined with ½×IC50 of OXP). Cells were incubated for 72 hr in a humidified atmosphere with 5% $CO_2$ in air at 37° C. Cell number was assessed by the MTT assay as described previously. The activities of drug combinations were established by comparing optical density readings from the treated wells with the control wells with no drug treatment, and data were expressed as a fraction unaffected (FU). The natures of drug-drug interactions were then assessed by calculating a combination index (CI) by using the median-effect equation (Chou et al., 1984, Adv Enzyme Regul. 22:27-55), where CI-values of 1 indicated additivity; CI<1 indicated synergy and CI>1 indicated antagonism.

Combination Studies: Fixing the Concentration of One Drug.

Median-effect analysis of combination requires the extrapolation of an IC50 value. Where this was not possible, the effect of combining drugs was explored by fixing the concentration of one drug (modulating agent) and testing its ability to influence the activity of the drug partner. Cells ($5 \times 10^4$/well) growing exponentially were reset in fresh culture medium and aliquoted into 96-well plates. ART or ATM were diluted in growth medium and added to the plates in a range of drug concentrations to allow determination of IC50. The effect on these IC50 values of co-culture with a sub-optimal concentration (~IC10) of GEM, THA or LEN was then tested. Cell numbers at 72 hr were assessed by the MTT assay as previously described. This enabled the assessment of the nature of any drug-drug interaction by comparing the IC50 for ATM and ART in the presence and absence of the combinatorial drug partner.

6.1.2 Results

ATM and ART Reduce Cell Number.

Concentration-dependent decreases in cell number were seen in all the cell lines cultured with both ART or ATM, apart from in PANC-1 (FIG. 1). MCF7 cells were most sensitive to the antimalarial drugs, with calculated concentrations required to reduce cell numbers by 50% (IC50) for ART and ATM of 44 µM and 0.5 µM respectively. Generally, ATM was more active than ART, which was most clearly highlighted when comparing the IC50 values (Table 1). IC50 values were taken from the cell viability curves and represent the concentration needed to reduce the cell population by half after 72 hours treatment with the drug. The IC50s for ATM were consistently lower than that of ART in all cell lines. Each value represents the mean and SDs of at least 3 separate experiments. Of particular note, in MJT3, where ART had no effect, ATM significantly reduced cell number. Similarly, HCT116 and SW480 were around 30× more susceptible to ATM than to ART. These reductions in cell numbers were not associated in increased cell death as assessed by trypan blue dye exclusion.

TABLE 1

Comparison of IC50 values obtained for ART and ATM in seven cell lines.

| IC50 (µM) | Artemisinin | Artemisone |
|---|---|---|
| Colon | | |
| HCT116 | 204 ± 88 | 9.5 ± 0.9 |
| SW480 | 156 ± 38 | 4.5 ± 1.6 |
| Melanoma | | |
| MJT3 | >1,000 | 30 ± 26 |
| KM | 101 ± 15 | 6.4 ± 2.1 |
| Pancreas | | |
| PANC1 | >1,000 | >1,000 |
| MiaPaCa3 | 31 ± 13 | 14 ± 10 |
| Breast | | |
| MCF7 | 44 ± 15 | 0.56 ± 0.17 |

ATM and ART Induce Cell Cycle Blockade.

Flow cytometric analyses revealed there was no increase in the apoptotic/sub-G1 phase of the cell cycle of HCT116, SW480 or MCF7 after culturing with ART or ATM (FIG. 2). However, there were cell cycle changes that were particular to each drug and cell line. Treating HCT116 cells with either ART or ATM did not alter the distribution of cells within the G1, S and G2 phases, which taken with the results of the proliferation assays, suggested a general blockade at all phases (FIG. 2). A similar cell cycle profile was seen in SW480 cells cultured with ATM. However, culturing SW480 cells with ART resulted in a significant decrease in the amount of cells in G1 (63±2.6% vs. 53±6.1% in untreated cells; p<0.05) and concomitant increases in the phases downstream of G1. This effect was reversed in MCF7 cells, with ATM causing a G1-selective blockade (83±5.5% vs. 63±4.40% in untreated cells; p=0.015), but a general arrest in all phases after culturing with ART (FIG. 2).

ART and ATM Affect Proteins that Regulate Cell Cycling.

Figure 3:
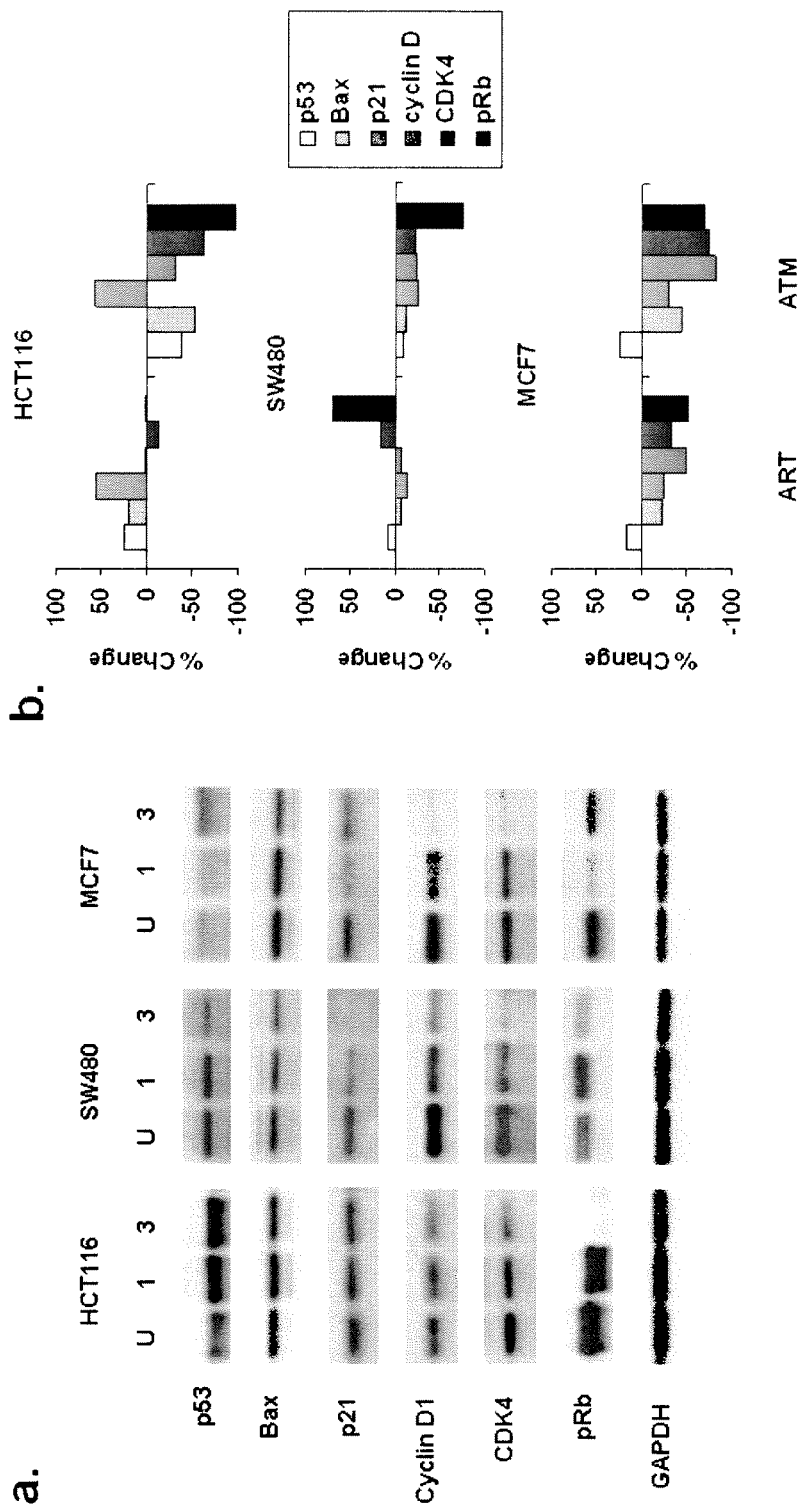

Whole cell lysates from cell lines cultured with ART or ATM were immunoprobed for the expression of key cell cycle regulatory proteins. Treatment with either drug significantly reduced the levels of cyclin D1 and its associated CDK 4 (FIG. 3). Although the ATM and ART were used at equi-active concentrations (~IC25), the former agent reduced these two cell cycle regulatory proteins to a greater extent compared to ART. Generally, these reductions correlated with reduced pRb expression, which were lower in ATM treated cells. Levels of the general CDK inhibitor $p21^{waf1\,cip1}$ were generally unchanged by treatment.

ART and ATM can Enhance the Effects of Some Chemotherapy.

Figure 4:
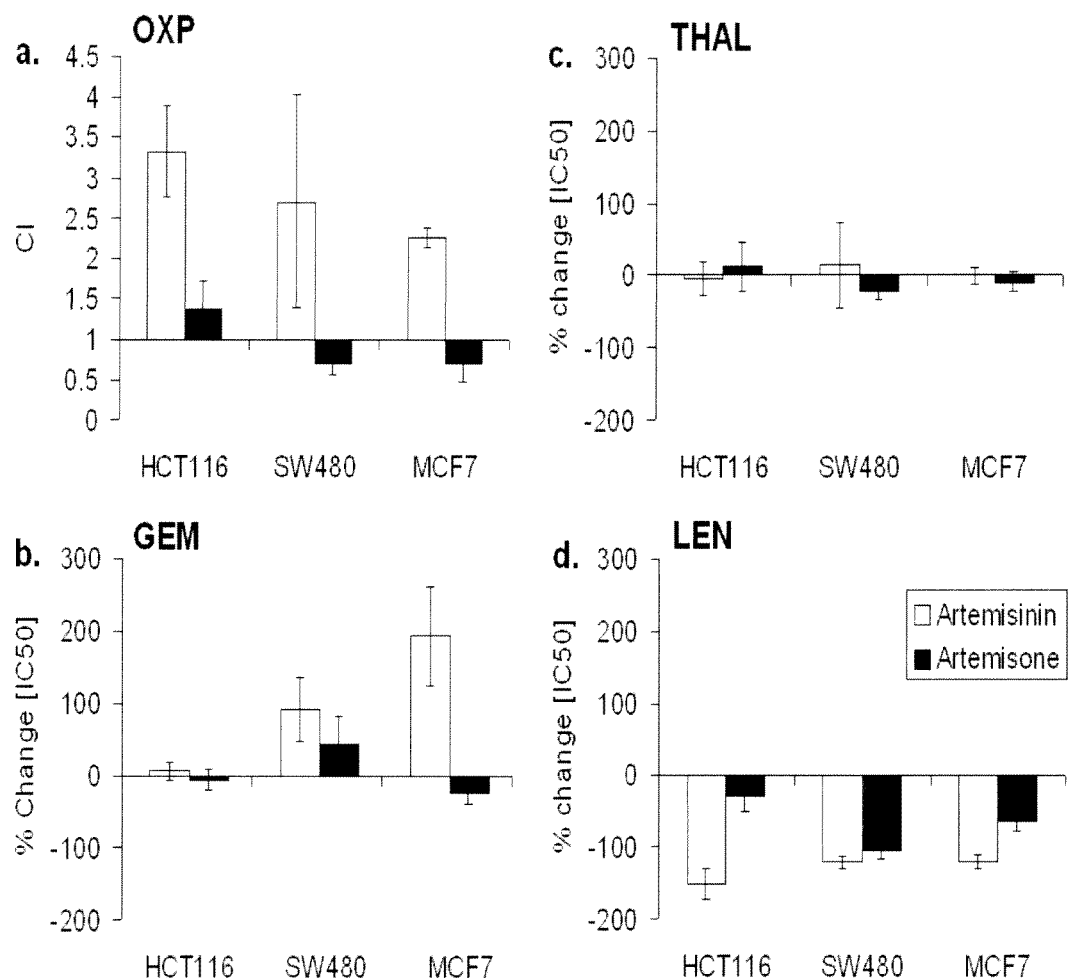

The benefits of combining ART and ATM with common chemotherapy were explored using a number of models. Benefit was indicated either by low CI-values or by decreases in IC50-values. Results showed ATM to be a better than ART when used in combination with OXP or GEM. Whilst combining ART with OXP resulted in CI-values in HCT16, SW480 and MCF7 of 3.3±0.57, 2.3±0.13 and 2.7±1.3 respectively, which were significantly different from a CI-value of 1 (p<0.05 in all cases), combining ATM with OXP results in an additive interaction (FIG. 4). Similar patterns to these were seen between GEM and ART/ATM, with ART interfering with the activity of GEM and ATM having no significant effect. Combinations with THAL resulted in no significant interaction, whilst genuine enhancement of drug activity was achieved when ART or ATM were combined with LEN (FIG. 4)

6.1.3. Discussion

This study was undertaken to investigate the anti-cancer properties of ATM, a novel and potent derivative of ART, in a panel of cell lines. The inventors had a particular interest in assessing their effects on cell proliferation and cell cycling, and in comparing these effects with those of the parental ART. Additionally, the activities of these agents when used in combination with existing chemotherapies were also assessed. The inventors showed that ATM was more active against cancer cell lines than ART both as a single agent and as a combinational partner, and that the effects were through disruptions to the cell cycle.

The first part of this investigation established, by MTT analysis, that both ART and ATM adversely affected cell number. However, the effect of ATM was much more profound, in that IC50 values for ATM were considerably lower than those for ART in all cell lines. IC50s were similar to those published previously with other cell lines and were within the range of clinically achievable plasma concentrations reported for other ARTds, which are typically in the millimolar range (Batty et al., 1996, *J. Chromatogr. B Biomed. Appl.* 677: 345-350). The increased activity between ATM and ART was most prevalent in the MCF7 breast cancer cell line, where IC50 was around 80-fold less for ATM than its precursor ART. Conversely, neither drug had an impact on the p53-mutant nor resistant PANC1 cell line, although it remains to be seen whether this resistance could be overcome by strategic combinational regimen involving ARTds. One of the most interesting findings was that ATM could significantly deplete cell number in cell lines seemingly resistant to ART, as was the case with MJT3 cells. The results also showed that the ability of ATM to reduce cell number in vitro was much greater than that of ART both in magnitude and breadth, with potent activity in breast, colon, pancreas and melanoma cancer lines. Parenthetically, ATM has previously been shown to be consistently more active against malarial parasites than other, more accessible ARTds (Ramharter et al., 2006, *Am. J. Trop. Med. Hyg.* 75: 637-639). One reason for this may be the superior bioavailability of ATM, which results in higher levels in plasma and sustained activity. Taken together, these results suggest that ATM may be more successful against cancer in in vivo studies than previously studied ARTds.

Trypan blue dye exclusion analyses conducted in parallel to the MTT assay showed both ART and ATM did not affect cell viability (data not shown), which suggested their effects were cytostatic rather than cytotoxic. For this reason, the inventors investigated the impact of the drugs on cell cycle distribution. Results revealed an absence of cell death (sub-G1 population) in cultures with ART or ATM, which was further supported by immunoblotting where no increase in the pro-apoptotic protein Bax was observed. Changes in the cell cycle were observed after treatment with the agents; specifically, cell cycle arrest as reported previously (Hou et al., 2008, *Clin. Cancer Res.* 14: 5519-5530; Efferth et al., 2003, *Mol. Pharmacol.* 64: 382-394; Beekman et al., 1997. *J. Nat. Prod.* 60: 325-330). These results showed that the compounds generally induced a simultaneous arrest at all phases of the cell cycle. However, in the case of MCF7 cells treated with ATM an accumulation of cells within the G1 phase was observed indicating a block exclusively at G1/S interface. Conversely, in the response of SW480 cells to ART there was a significant decrease in the number of cells in G1 and a trend towards increased numbers in S and G2, signifying a cell cycle block downstream of G1.

Having seen alterations in the number of cells at the differing points in the cell cycle, the inventors next investigated the molecular basis of these changes using protein immunoblots. Cell cycle transition is tightly regulated by a series of proteins that coordinate transitions between phases. Of these, the inventors focussed on those regulating G1-to-S passage as they have been shown to be affected by the ARTds (Li, et al., 2001, *Bioorg. Med. Chem. Lett.* 11: 5-8). The protein that directly controls this is pRb. A consequence of losing this protein is a block in G1. These results revealed a dramatic reduction in levels of pRb in each cell line in response to ATM, and in MCF7 cells only after culture with ART. This decrease in pRb was always associated with a decrease in the levels of its regulatory proteins CDK4 and cyclin D1, which maybe mediated by sp1 interaction (Willoughby et al., 2009, *J. Biol. Chem.* 284: 2203-2213). Notably, pRb was increased in SW480 cells cultured with ART, which correlated with the decrease in the number of cells in the G1. The diverse effects of ART and ATM support the notion that ARTds have multiple modes of action. Previously it has been shown that ARTds can affect the cell cycle in a p53-dependent or independent manner (Efferth et al., 2003, *Mol. Pharmacol.* 64: 382-394). These data supports this in that cytostasis was achieved with or without up-regulation of p53 and p21. Obstruction of the cell cycle can be considered to be one of the most effective strategies in the control of tumour growth, and with the effects observed in the present study ATM may become an important compound in the armoury of agents available to achieve this.

Cancers are characterised by multiple genetic defects which may reduce the efficacy of single agent chemotherapy. Therefore, by using combination therapies to hit either diverse pathways or mutually exclusive points on the same pathway, the chance of cancer cells evading treatment can be reduced. This underlies the idea of combination strategies where drugs are used simultaneously to achieve an effect that is greater than the sum of its parts (Liu W M. 2008, *Curr Clin Pharmacol.* (2): 108-17). However, care needs to be taken when choosing combinations to minimise undesired interactions. Evidence from other studies suggests that some ARTds may potentiate other, more established treatments (Singh et al., 2005, *Anticancer Res.* 25: 4325-4331; Chen et al., 2009, *J. Cell Mol. Med.* 13: 1358-1370; Zhou et al., 2009, *Cancer Chemother. Pharmacol.* 66(1):21-9).

The inventors therefore tested the ability of ART and ATM to sensitise HCT116, SW480 and MCF7 cells to OXP and GEM. The drugs selected are established treatments for colon or breast cancer. Also, these drugs affect cell cycle and influence p53 or p21 (Hata et al. 2005, *Mol. Cancer. Ther.* 4: 1585-1594; Tolis et al., 1999, *Eur. J. Cancer,* 35: 796-807). Thalidomide (THAL) and lenalidomide (LEN) were selected on the basis of targeting p21 (Escoubet-Lozach et al., 2009, *Cancer Res.* 69: 7347-7356).

There are a number of models used to investigate the benefits of combining drugs. One approach that has previously been used is the median-effect equation to generate CI-values. These values give an indication of the 'worth' of a combination with CI>1 signifying antagonism and CI<1 suggesting enhancement of effect between the compounds. These calculations rely on sigmoidal growth inhibition curves being generated for each compound; however, the response curves for GEM, THAL or LEN did not meet this criterion, and hence, the median effect equation could not be used. Consequently, the inventors used small sub-active concentrations of each of the drugs in an attempt to modulate the effect of ART and ATM using a model that has been described previously (Liu et al., 2008 Leuk Lymphoma. 49(9):1800-9).

The present study suggests that ATM has a much better combination portfolio than ART. Generally, ART-combinations were mostly antagonistic, whilst non-antagonistic effects were prevalent when ATM was used. Specifically, the CI-values for combinations with ATM and OXP were significantly lower than for those for ART and OXP. Therefore, as ART has previously been shown to be advantageous in combinational therapies, these results suggest that ATM has the potential to be more so.

In conclusion, ARTds are a class of agent approved for use against malarial parasites that are resistant to most other treatments. There is evidence that they affect a number of different pathways and have multiple targets in malarial parasites. If these lessons are applied to cancer, then, due to the variety of ways that these compounds can act on and disrupt cancer cells, such as inducing apoptosis and disrupting the cell cycle, they should hinder disease progression, and thus, become important players in cancer treatment. It is believed that this is the first time ATM has been used against tumour cell lines. The inventors have shown that ATM has stronger activity against cancer than other ARTds. Overall, the possibilities of the ART class are promising in cancer applications.

6.2 Anti-Proliferative Effects of Artesunate and Lenalidomide

This example describes the anti-proliferative effect of Artesunate (ART) in a panel of cancer cell lines in vitro, and investigate possible interactions between ART and established chemotherapy agents by using an array of more detailed methodologies. This study tested the general concept that drugs with similar mechanistic profiles to ART could be used in combination to enhance the overall susceptibility of cancer cells to these drugs.

6.2.1. Methods

Drugs.

Artesunate (ART: Pharmacy, St George's Hospital (SGH), UK) and lenalidomide (LEN: Celgene Corp., Summit, N.J., USA) were both dissolved in dimethyl sulphoxide, and gemcitabine (GEM: SGH) and oxaliplatin (OXP: Sigma Ltd., Poole, Dorset. UK) in phosphate buffered saline (PBS). All drugs were reconstituted to a concentration of 10 mM, and stored at −20° C. for no longer than 4 weeks.

Cell Culture.

The human cancer cell lines; MCF7 (breast), HCT116 (colon) and A549 (lung) (Cancer Research UK, London, UK), were grown in either DMEM (Sigma) or RPMI (Sigma) media supplemented with 10% foetal bovine serum, 2 mM L-glutamine, 1% penicillin/streptomycin. All cell lines were incubated in a humidified atmosphere with 5% $CO_2$ in air at 37° C., and only cells with a passage number <10 were used in the experiments.

A HCT116 cell line variant that possessed a large population of cells that exhibited a ploidy greater than 4n was developed by culturing HCT116 cells in standard growth medium for 3-months and at passages >30. This extended-passage cell line, was designated $HCT116^{poly}$, had a fraction of cells with a higher DNA content, which displayed growth characteristics and doubling times that were similar to the parent HCT116 ($HCT116^{norm}$).

Proliferation Assays.

To study the effect of each agent on cell growth, cells growing exponentially were added to 96-well plates at a density of $3 \times 10^4$/well. Drugs (0.1-100 µM) were then added to the wells, ensuring an equal volume of 200 µl across the plate. Cell number was measured at 72 hr using a standard methylthiazoletetrazolium (MTT)-based assay without modifications as described previously (Gordi et al., 2004, Toxicol. Lett. 147: 99-107). Briefly, MTT (Sigma) was added to each well to give a working concentration of 0.4 mg/ml, and plates returned to the incubator for a further 1 hr. After this time, the medium was aspirated off, 200 µl of DMSO was then added to each well, and plates agitated gently for 5 min before measuring optical density at 540 nm in each well.

Flow Cytometric Analysis of the Cell Cycle.

Cells were cultured with ART (1-100 µM) for 72 hr. before fixing in 70% (v/v) ethanol in PBS. Following an incubation period of at least 30 min. cells were washed and re-suspended in a DNA staining solution (1 mg/ml propidium iodide and 1 ng/ml RNAse A (both Sigma). Acquisition of data was performed within 1 hr using a Becton Dickinson FACSCalibur (BD Biosciences), and gating on fluorescence width and area was employed to remove doublet artefacts and to discriminate cells from debris. Ten thousand cells were analysed, and the percentages of cells in G1, S and G2/M phases were determined using the cell cycle analysis program WinMDI CellQuest v2.9 (http://facs.scripps.edu/software.html).

Immunoblotting Analysis.

Cells were harvested and total cellular protein was solubilised in lysis buffer (New England Biolabs, Hitchin, UK) and resolved by Tris-glycine electrophoresis using a 4-12% bis-tris gradient-gel. Following transfer of proteins to 0.45 µm nitrocellulose membranes, blocking was performed in 5% (w/v) non-fat milk in TTBS [0.5% (v/v) Tween-20 in TBS (50 mM Tris, 150 mM NaCl, pH 8.0)]. Primary antibody probing was performed with anti-p21, anti-Bax, anti-CDK4, anti-cyclin D1, anti-pRb or anti-cyclin B1. All primary antibodies were obtained from New England Biolabs (Hitchin, UK) and used at a dilution of 1:1,000, unless stated otherwise. Anti-GAPDH was used as a loading control (1:2,000—New England). Following three washing steps in TTBS, horseradish peroxidase-conjugated anti-species IgG was used as the secondary antibody (Amersham Biosciences Ltd., Little Chalfont, UK). Bands were visualised by the ECL-plus detection system (Amersham).

Combination Studies: Fixing the Ratio of the Concentration of the Drugs.

The combination studies followed an approach previously described (Gordi et al., 2004, Toxicol. Lett. 147: 99-107). $HCT116^{norm}$, A549, MCF7 and $HCT116^{poly}$ cells ($5 \times 10^4$/well) growing exponentially were reset in fresh culture medium and aliquoted into 96-well plates. ART was the primary drug partner and combined with OXP at an equal ratio of their respective IC50 (eg. ½×IC50 of ART was combined with ½×IC50 of OXP). Fixing this ratio also kept constant the amount of one drug respective to the other. For instance, ART was combined with OXP at a constant ratio of 1:2.5. Cells were incubated for 72 hr in a humidified atmosphere with 5% $CO_2$ in air at 37° C. Cell number was assessed by the MTT assay as described previously. The activities of drug combinations were established by comparing optical density readings from the treated wells with the control wells with no drug treatment, and the natures of drug-drug interactions then assessed by calculating a combination index (CI) by using the median-effect equation, where CI-values of 1 indicated additivity; CI<1 indicated synergy and CI>1 indicated antagonism.

Combination Studies: Fixing the Concentration of One Drug.

Median-effect analysis of combination requires the extrapolation of an IC50-value. Where this was not possible, the inventors explored the effect of combining drugs by fixing the concentration of GEM or LEN (modulating agent) and testing its ability to influence the activity of ART (drug partner). Cells ($5 \times 10^4$/well) growing exponentially were reset in fresh culture medium and aliquoted into 96-well plates. ART was diluted in growth medium and added to the plates in a range of drug concentrations to allow determination of IC50. The effect on these IC50 values of co-culture with a sub-optimal concentration (~IC20) of GEM or LEN was then tested. Cell numbers at 72 hr were assessed by the MTT assay as previously described. This enabled the assessment of the nature of any drug-drug interaction by comparing the IC50 for ART in the presence and absence of the combinatorial drug partner.

Recovery Studies.

The effect of recovery from the drug was studied by studying the impact that removing drugs from cells would have on cell growth and survival. A549, MCF7 and $HCT116^{poly}$ cells growing exponentially were reset at $5 \times 10^4$/well, and allowed to establish for 24 hr, before adding 30µM ART. Following 2-days culture, media were aspirated and the cells washed twice with PBS. Fresh culture medium was then returned to the cells with or without ART (30 µM), and incubated 2-days further. Cell number and viability were then assessed on days 2 and 4; with percentages of live and dead cells discriminated by trypan blue dye exclusion.

6.2.2. Results

ART Reduces Cell Number by being Both Cytotoxic and/or Cytostatic.

Three commonly used anti-cancer agents were selected for investigation on the basis of their activities in the cancer types studied, as well as on preliminary studies that showed similar modes of action. There were dose-dependant reductions in cell numbers as established by MTT scores in all cell lines cultured with ART, CPM, LEN and GEM, with IC50 values showing that A549 cells were generally less sensitive to the cytotoxic effects of the four drugs (Table 2). The values were established by the MTT assay, and represent the means and SDs of at least five independent experiments. The sub-optimal concentrations used in the combination experiments were decided by more detailed analyses of emax-modelling of data around the top of the dose-response curve, and were those that caused no more than 10% cell death.

TABLE 2

IC50-values (μM) at 72 h for ART, LEN, GEM and OXP in A549, HCT116$^{norm}$ and MCF7 cell lines.

| | Cell line | | |
|---|---|---|---|
| IC50 (μM) | A549 | HCT116$^{norm}$ | MCF7 |
| Artesunate | 9.8 ± 1.7 | 1.92 ± 0.35 | 2.3 ± 0.94 |
| Lenalidomide | >100 | >100 | >100 |
| Gemcitabine | 14 ± 1.6 | 5.2 ± 2.02 | 1.9 ± 0.75 |
| Oxaliplatin | 6.2 ± 0.95 | 4.05 ± 1.8 | 6.1 ± 1.1 |

The reductions in cell numbers caused by ART were recapitulated by cell counting using microscopy and viability discrimination by trypan blue exclusion (FIG. 5a). This also revealed that the reductions in cells numbers in HCT116 cells seen after culturing with ART was associated with a dose-dependent reduction in cell viability. However, there were no decreases in the cell viability of A549 and MCF7 cells cultured with ART, which suggested a cytostatic effect (FIG. 5a).

Flow cytometric analyses revealed culturing cells with ART induced clear dose-dependent increases in the sub-G1 (apoptotic/debris) population in HCT116 cells, but no changes in A549 and MCF7 cells (FIG. 5b). There were no dramatic changes to any of the cell cycle phases in A549 cells, which supported the overall notion of a simultaneous blockade in cell progression at all phases of the cell cycle. A similar broad-spectrum cell cycle arrest was also seen in MCF7 cells cultured with higher concentrations of ART (>30 μM). However, flow cytometry showed significant increases in the percentage of cells within G1 and concomitant decreases in cell within the S-phase of the cell cycle, which pointed to more specific blockades at the G1-to-S and G2-to-M transitional points with concentrations <30 μM.

ART Alter Proteins that Regulate G1 Transit.

To investigate the effect of ART on cell proliferation, whole cell lysates obtained from cell lines cultured with ART were immunoprobed for CDK4 and cyclin D—the first-line protagonists that initiate and drive cells through the restriction point. Both proteins, upon treatment with ART, were reduced in a dose-dependent manner (FIG. 6). There were also concomitant reductions in pRb at similar concentrations, which was clearest in A549 and MCF7 cells. The level of expression of the phosphatase p21$^{waf1/cip1}$ was dramatically increased in HCT116 and MCF7 cells but unchanged in A549 cells. This was most clearly demonstrated in the densitometry graphs (FIG. 6).

ART Acts Additively with Chemotherapy to Reduce Cell Number and Viability.

The inventors used MTT assays to establish drug-combination activity, and calculated CI-values to determine the nature of drug-drug interactions. These computations require the tested drugs to respond in a dose-dependent effect, which permits the calculation/extrapolation of IC50-values that are shown in Table I. However, these values could not be generated for LEN and were not used this model. CI-values were generated from data that were generally no different from 1, which suggested an additive interaction of ART with GEM or with OXP (FIG. 7a). There was the faintest hints of antagonism with ART and GEM combinations in HCT116, but this did not reach significance (p=0.073).

The Cytotoxic Effects of ART is Enhanced by LEN.

The lack of a dose-response in the cells rendered the primary model of drug-drug interaction ineffectual for combinations of ART with LEN. For this reason the inventors next tested the ability of LEN to sensitise cells to ART. These combinatorial analyses were performed in all the cell lines using a smaller concentration of LEN (0.1 and 1 μM). These concentrations had little effect on cell numbers and viabilities. Results showed that this sub-toxic amount of LEN had no significant impact on the response of HCT116$^{norm}$ cells to ART. However, these modulatory does of LEN significantly enhanced the effect of ART in A549 and MCF7 cells as indicated by a fall in their IC50-values (FIG. 7b).

Generation of ART-Resistant Polyploid HCT116 Cells.

HCT116 cells that were passaged and maintained using standard cell culture procedures for ~3 months spontaneously developed a polyploidy phenotype. These cells, designated HCT116$^{poly}$ exhibited similar growth characteristics, with a population-doubling time of about 28 h (27.6±5.9 for HCT116poly vs. 28.2±3.9 for HCT116$^{norm}$). The percentage of HCT116$^{poly}$ cells located within the polyploid continuum (where ploidy was >2) was increased by nearly 3-fold (39±10% vs. 14±1.4%; p<0.001), with clear definitions of cells in 8n, 16n and 32n (FIGS. 8a, 8b).

Figure 8:
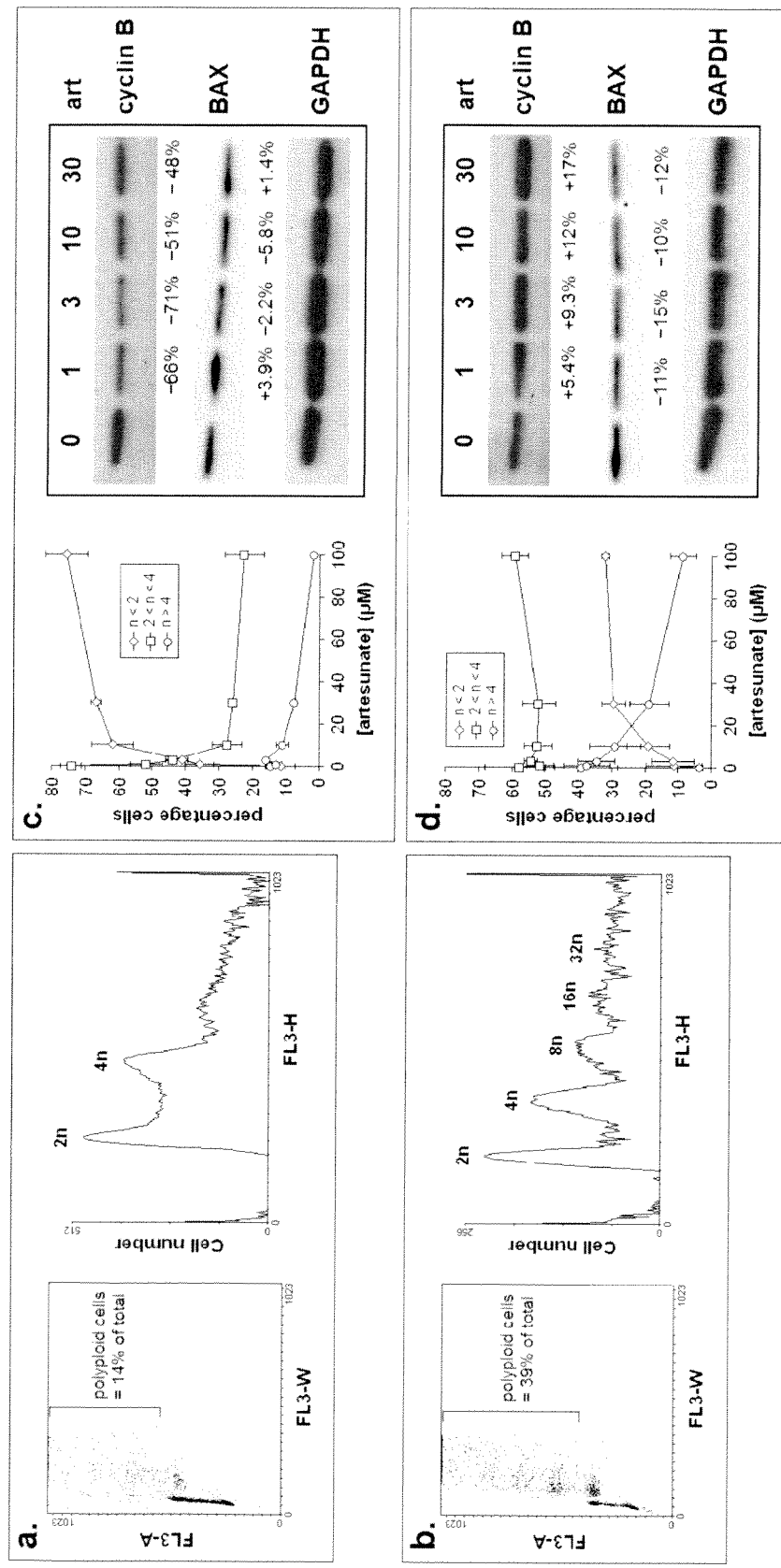

The sensitivity of HCT116$^{poly}$ cells to ART was noticeably reduced, with an IC50-value of 39±2.6 μM, which was significantly higher than that seen in the parental HCT116$^{norm}$ cell (1.9±0.35 μM; p<0.001) (FIGS. 5a, 8c, 8d). Flow cytometric analyses of cells following culturing with ART revealed a dose dependent increase in the sub-G1 population of cells, which was associated with a reduction in the polyploid fraction, a reduction in the % G1 events, and an increase in the % G2 cells (FIGS. 5b, 8c, 8d). The molecular profile of HCT116$^{poly}$ cells cultured with ART was generally the same as that of the HCT116$^{norm}$ (FIG. 6). However, differences were seen with cyclin B (reduced in HCT116$^{norm}$ but unchanged in HCT116$^{poly}$) and BAX (unchanged in HCT116$^{norm}$ but decreased in HCT116$^{poly}$) (FIGS. 8c, 8d).

ART Cytotoxicity in HCT116$^{poly}$ Cells is Enhanced by a Recovery Phase.

Figure 9:
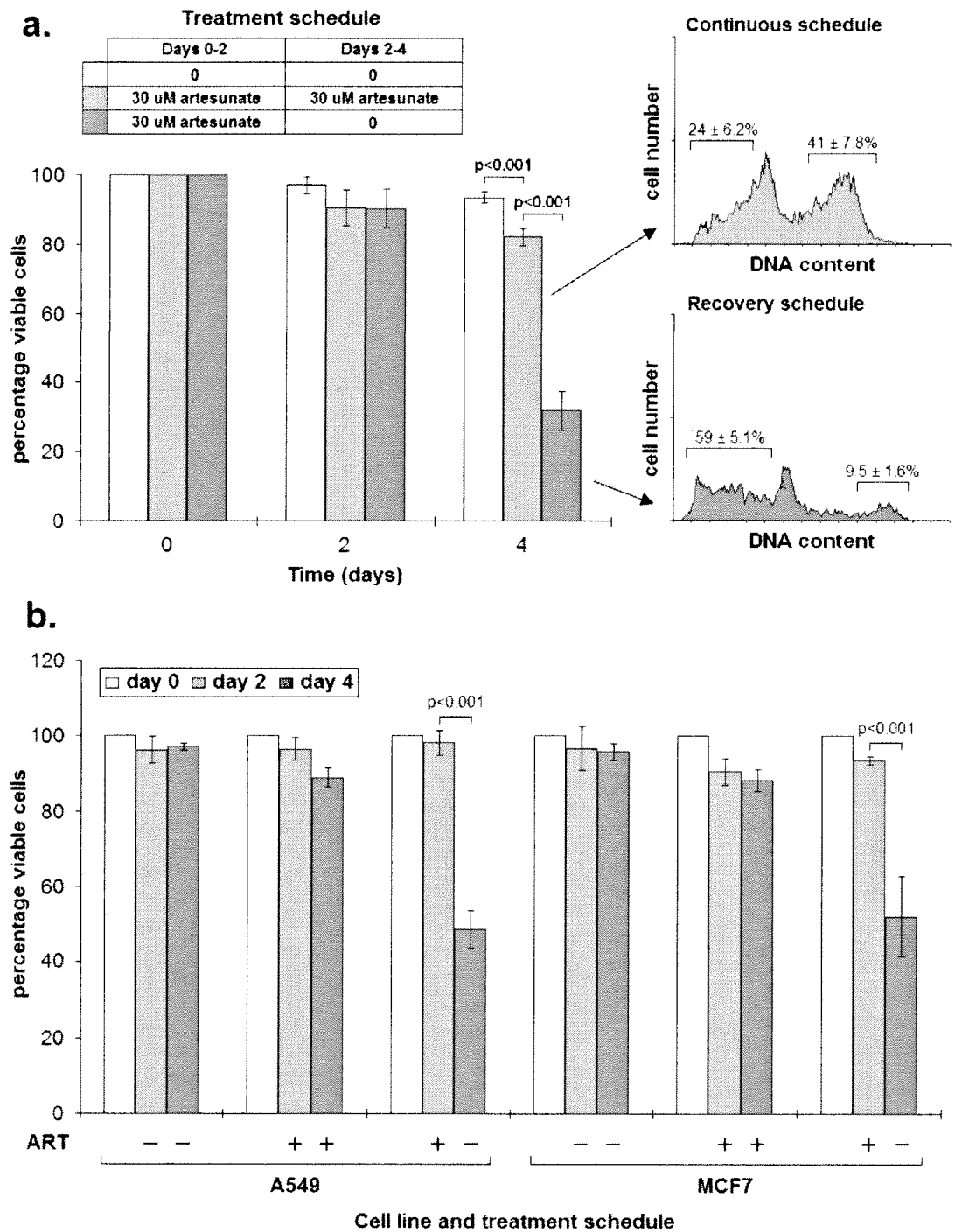

To investigate whether the G2-block observed in HCT116$^{poly}$ was preventing cell death (Adjuik et al., 2004, Lancet, 363(9402):9-17), and was inadvertently maintained in the presence of ART, these cells were cultured in 30 μM ART for 2-days before removal of the drug and recovery in drug-free medium for a further 2 days. Results showed re-culturing ART-treated HCT116$^{poly}$ cells in drug-free medium caused significant decreases in cell viability (FIG. 9a). This was associated with an easing of the G2-block, and concomitant increases in the sub-G1 (apoptotic/dead) cell population (FIG. 9a).

Similar results were seen in both A549 and MCF7 cells following an equivalent treatment-recovery schedule, with significant losses in cell viabilities after re-culturing ART treated cells in drug-free medium, compared to cells cultured in 30 μM ART continuously for 4-days (p<0.001) (FIG. 9b).

6.2.3. Discussion

These studies were undertaken as part of larger remit to investigate whether or not immunotherapies could enhance the activities of other modalities and, thus, improve the outcome and quality of life in cancer patients. An avenue of research has involved exploratory studies with drugs that possess anti-cancer properties, but are not typically used in an oncological setting. These drugs have established therapeutic roles in their respective indications, and are therefore safe to use; however, their potential in other disease types may not have been explored thoroughly. In the current study, the inventors specifically investigated the anti-proliferative effects of the malarial compound ART on a panel of cancer cell lines. By using in vitro models, the inventors assessed its effects on cell growth and survival, and established the value of drug-combination strategies that included its use. In summary, the results showed ART possessed good anti-tumour effects, which were associated with modifications to cell cycle functionality. Furthermore, efficacy could be enhanced by combining ART with other drugs, and by adapting treatment schedules to include drug-free periods.

In the first part of the current study, the inventors assessed the activity of ART in a small panel of cancer-derived cell lines, and showed through MTT assays, a dose-dependent reduction in cell numbers. A reduction in cell number can be a consequence of active cell kill or inhibition of proliferation. Consequently, the inventors performed cell counting using light microscopy supported by trypan blue exclusion to discriminate viable from non-viable cells. A reduction in cell viability was seen only in HCT116$^{norm}$ cells, which suggested ART was cytotoxic in this cell line. Conversely, no changes to the viability of A549 and MCF7 but significant reduction in the number of cells as determined by cell counting, suggested a cytostatic response to ART. This deduction was further supported by flow cytometric analysis of cell cycle distribution that revealed ART caused no significant changes to the cell cycle, which suggested a simultaneous arrest at all phases of the cell cycle. This effect has been observed with other derivatives of artemisinin (Hou et al., 2008, *Clin Cancer Res*, 14:5519-30), and associated with down-regulation of cyclins and CDKs. The results recapitulated these earlier results showing clear and significant increases in p21$^{waf1/cip1}$ and concomitant decreases in cyclin D1 and/or CDK4. These proteins are central regulators of transition through G1-initiation, and their reduced levels coupled with loss of pRb, indicated disruption to G1 and S transit. G2-cycling was also affected as indicated by a reduction in cyclin B1. Taken together, ART was a potent cell cycle inhibitor.

The actions and activities of drugs that target cell cycling are interlinked with the ploidy status in the effector cell (Castedo et al., 2006, *Ann N Y Acad Sci*, 1090:35-49). In fact, uncoupling DNA synthesis from cytokinesis can give rise to endo-replication and then polyploidy—a phenotype that is common in cancer cells (Ganem et al., 2007, *Curr Opin Genet Dev*, 17:157-62). Synchronisation of cell cycle events is achieved by cyclins and their partner CDKs; and disrupting these regulatory proteins, particularly CDK1/cyclin B can lead to polyploidy. Cell cycle inhibitors/modifiers work through these same proteins, and consequently activity may be influenced by the condition of the ploidy. For this reason, the inventors induced polyploidy in HCT116$^{norm}$ cells and assessed the activity of ART in this variant. Methodologically, polyploidy was induced in the HCT116$^{norm}$ cell line, which is a microsatellite unstable line with MLH1 deficiencies (Chang et al. 2000 *J Biol Chem*, 275:29178: Abdel-Rahman et al. 2001. *Proc Natl Acad Sci*. 98:2538-43: Plaschke et al., 2004, *Cancer Res*, 64:864-70) by extending the duration of its maintenance for over 3 months. Repeated passage of cells can increase the frequency of polyploidy in cells as a result of increased stress (Baatout S. 1999, *Hematol Cell Ther*, 41:169-70; Lee et al., 2009, *Genes Dev*, 23:2461-77), and the method used in the current study consistently resulted in cells with polyploidy features. These HCT116$^{norm}$ cell variants were designated HCT116$^{poly}$, and hyperploidy was indicated by a distinct cell continuum above the G1/S/G2/M group of cells specified by FL3-A vs. FL3-W analysis. This was confirmed by Giemsa-banding (data not shown), which reported the presence of cells with chromosome numbers >45 (normal range: 43-45) (Abdel-Rahman et al., 2001, *Proc Natl Acad Sci*, 98:2538-43).

Results indicated that the ART continued to reduce cell numbers in HCT116$^{poly}$ cells. However, the nature of this reduction had now switched to a cytostatic one; with the magnitude of cell death (indicated by % viable cells) being significantly reduced. Flow cytometry showed that the polyploidy fraction of cells was reduced by culturing with ART, which was mirrored by a small increase in the sub-G1 population. However, strikingly, cells within the normal ploidy-range were now blocking in G2. Furthermore, western blotting showed cyclin B levels, which were down regulated in HCT116$^{norm}$ or cells, were now unchanged after treatment in HCT116$^{poly}$. Taken together, these results suggested that alterations to HCT116$^{norm}$ cells that rendered them polyploidy also made them less sensitive to ART. This resistance however, was not observed in the polyploidy fraction of cells, but only in cells with a normal ploidy. This is reassuring considering a large proportion of cancers are associated with a level of hyperploidy (Ganem et al., 2007, *Curr Opin Genet Dev*, 17:157-62). Resistance in this fraction was associated with a G2-blockade, and appeared to be specific to ART, as the sensitivities to GEM and OXP were similar in HCT116$^{poly}$ and HCT116$^{norm}$ (15 and 5.8 μM vs. 19 and 5.3 μM, in HCT116$^{poly}$ and HCT116$^{norm}$, respectively) (data not shown).

Reduced sensitivity to chemotherapy associated with a G2-blockade has been reported previously (Liu et al. 2002, *Eur J Cancer*, 38:842-50; Liu et al., 2003, *Cancer Chemother Pharmacol*, 51:291-6). Specifically, the protracted presence of a drug-induced and maintained cell cycle arrest could prevent cell death. However, cytotoxicity was restored by adapting treatment schedules to include drug-free periods, which allowed easing of the G2-block and re-engagement of cell death. For this reason, the inventors next tested the effect of a washing step in treatment schedules to see if sensitivity to ART could be improved in HCT116$^{poly}$ cells. Results showed that allowing cells to grow in drug-free medium following an initial exposure to ART resulted in a significantly greater level of cytotoxicity compared to cells maintained in ART for the same duration. Furthermore, these results were subsequently recapitulated in A549 and MCF7 cells, where the removal of ART from treated cells and maintenance in drug-free medium resulted in significant reductions in cell viability.

The idea of combining drugs in therapeutic regimens is to achieve an overall effect that is greater than the sum of the individual effects of each agent (Liu W M., 2008, *Curr Clin Pharmacol*, 3:108-17). This is particularly important as a number of novel therapeutic modulators appear to be ineffectual cytotoxic agents on their own, with activity greatest when utilised with a partner. For example, drugs that interfere with PI3-kinase at the level of AKT do not cause cell death directly, but instead reduce resistance to other cytotoxic agents (Martelli et al., 2003, *Leukemia*, 17:1794-805; Neri et al., 2003, *Mol Cancer Res*, 1:234-46). Furthermore, the possibility of combining drugs without a loss of effect (antagonism) would be clinically worthwhile, as a similar level of activity could be achieved at lower doses. The incidence of drug-mediated adverse events could also be minimised because of this dose reduction.

Drug combinations that involve ART have been reported in vitro, which show value in this approach, both as a sensitising agent to chemotherapy in solid tumours (Hou et al., 2008, Clin Cancer Res, 14:5519-30; Sieber et al., 2009, Int J Oncol, 35:149-58) and as a synergistic partner with doxorubicin in leukaemia (Efferth et al., 2007, PLoS One, 2:e693). Thus, the inventors next explored the value of using ART in combination with the cytotoxic agents GEM and OXP by using median-effect algorithms to generate CI-values, which allowed for the assessment of the nature of any interactions between ART and cytotoxic agent. Results showed interactions to be additive in nature as CI-values were hovering around 1, and suggested GEM and OXP in combinations did not antagonise the functions of each other. Indeed, further analysis showed that to achieve ~50% cell kill in HCT116$^{norm}$ cells, 1.9 μM ART or 4.0 MμOXP would be required if used separately; compared to just 0.65 μM and 1.6 μM for ART and OXP respectively, when used simultaneously.

In addition to conventional chemotherapies, the inventors also combined ART with the immunomodulatory drug lenalidomide. Both agents are multi-modal and efficacious in their disease type. Both are immune modulators, anti-angiogenic and anti-metastatic, and affect cells at the level of intracellular signalling such as MAPK/ERK. NF-κB and p21$^{waf1/cip1}$ (Li et al. 2009, Int J Hematol. 90:513-21). These pathways are examples of some that are commonly dysregulated in neoplasia. The drugs with a diverse repertoire of activity on intracellular processes would be therapeutically worthy (Liu et al., 2008, Curr Clin Pharmacol, 3:108-17). The current study results showed that the activity of ART, as indicated by IC50-values, was enhanced by the addition of a low concentration of LEN, which had no effect on cell number and proliferation. For example, in A549 cells, the IC50 of ART in the presence of 1 μM LEN was reduced by 48% (IC50: 5.1±0.61 vs. 9.8±1.7 in cells cultured with ART alone; $p<0.001$). Parenthetically, this model, which involved modifying the activity of the primary cytotoxic agent with a subactive concentration of the modulating drug-partner, has been proposed and described previously in combination cases where one drug is ineffectual with regards to affecting the final readout (Gravett et al., 2010, Cancer Chemother Pharmacol, [Epub ahead of print]; Liu et al., 2008, Curr Clin Pharmacol, 3:108-17; Liu et al., 2008, Leuk Lymphoma, 49:1800-9).

The current study has reinforced a possible application for ART in a cancer therapy setting, not only as a single agent, but also in combination with some chemotherapy agents. This in vitro study highlights impressive anti-proliferative activity in a small panel of cell lines, and complements an ongoing randomised tolerability and efficacy study of oral ART in patients with colorectal carcinoma. The in vitro study also describes the effects of ART on the cell cycle, and presents data that shows restoration of cytotoxicity in an ART-resistant cell by adopting a pulsed-schedule.

All of the references cited herein are incorporated by reference in their entirety. While the invention has been described with respect to the particular embodiments, it will be apparent to those skilled in the art that various changes and modifications may be made without departing from the spirit and scope of the invention as recited by the appended claims.

The embodiments provided herein described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed:

1. A method of treating cancer, wherein the method comprises administering 3-(4-amino-1-oxo-1,3-dihydro-isoindol-2-yl)-piperidine-2,6-dione, and administering artemisinin or a derivative thereof, wherein the cancer is breast, colon or lung cancer, wherein the artemisinin derivative is artesunate or artemisone, and wherein the combination exhibits a synergistic effect.

2. The method of claim 1, wherein the artemisinin or derivative thereof is administered orally.

3. The method of claim 1, wherein 3-(4-amino-1-oxo-1,3-dihydro-isoindol-2-yl)-piperidine-2,6-dione is administered orally.

4. The method of claim 3, wherein 3-(4-amino-1-oxo-1,3-dihydro-isoindol-2-yl)-piperidine-2,6-dione is administered in the form of a capsule or tablet.

5. The method of claim 1, wherein 3-(4-amino-1-oxo-1,3-dihydro-isoindol-2-yl)-piperidine-2,6-dione is administered in an amount of from about 5 to about 25 mg per day.

6. The method of claim 1, wherein the artemisinin or derivative thereof, and 3-(4-amino-1-oxo-1,3-dihydro-isoindol-2-yl)-piperidine-2,6-dione are administered at the same time.

7. The method of claim 1, wherein the artemisinin or derivative thereof, and 3-(4-amino-1-oxo-1,3-dihydro-isoindol-2-yl)-piperidine-2,6-dione are administered sequentially.

* * * * *